United States Patent
Longo et al.

(10) Patent No.: US 12,285,453 B2
(45) Date of Patent: Apr. 29, 2025

(54) FASTING-MIMICKING DIET PROMOTES CANCER-FREE SURVIVAL IN ACUTE LYMPHOBLASTIC LEUKEMIA MODELS

(71) Applicant: UNIVERSITY OF SOUTHERN CALIFORNIA, Los Angeles, CA (US)

(72) Inventors: Valter D. Longo, Playa del Rey, CA (US); Roberta Buono, Newport Beach, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 17/539,726

(22) Filed: Dec. 1, 2021

(65) Prior Publication Data

US 2022/0168372 A1     Jun. 2, 2022

Related U.S. Application Data

(60) Provisional application No. 63/119,922, filed on Dec. 1, 2020.

(51) Int. Cl.

| | |
|---|---|
| A61K 36/185 | (2006.01) |
| A23L 33/00 | (2016.01) |
| A23L 33/115 | (2016.01) |
| A23L 33/17 | (2016.01) |
| A61K 31/155 | (2006.01) |
| A61K 31/436 | (2006.01) |
| A61K 31/4706 | (2006.01) |
| A61K 31/573 | (2006.01) |
| A61P 35/02 | (2006.01) |

(52) U.S. Cl.
CPC .......... *A61K 36/185* (2013.01); *A23L 33/115* (2016.08); *A23L 33/17* (2016.08); *A23L 33/30* (2016.08); *A61K 31/155* (2013.01); *A61K 31/436* (2013.01); *A61K 31/4706* (2013.01); *A61K 31/573* (2013.01); *A61P 35/02* (2018.01)

(58) Field of Classification Search
None
See application file for complete search history.

(56) References Cited

U.S. PATENT DOCUMENTS

| | | |
|---|---|---|
| 11,284,640 B2 * | 3/2022 | Brandhorst .............. A23L 2/52 |
| 2011/0118528 A1 | 5/2011 | Longo et al. |
| 2013/0045215 A1 | 2/2013 | Longo et al. |
| 2013/0316948 A1 | 11/2013 | Longo |
| 2014/0112909 A1 | 4/2014 | Longo et al. |
| 2014/0227373 A1 | 8/2014 | Longo et al. |
| 2014/0328863 A1 | 11/2014 | Longo |
| 2015/0004280 A1 | 1/2015 | Longo et al. |
| 2015/0133370 A1 | 5/2015 | Longo |
| 2015/0250771 A1 | 9/2015 | Longo et al. |
| 2016/0324193 A1 | 11/2016 | Longo et al. |
| 2018/0228196 A1 | 8/2018 | Le Fur et al. |
| 2018/0228198 A1 * | 8/2018 | Brandhorst ............ A23L 33/20 |
| 2020/0010562 A1 | 1/2020 | Longo et al. |
| 2020/0146320 A1 | 5/2020 | Longo |

FOREIGN PATENT DOCUMENTS

| | | |
|---|---|---|
| WO | 2011/050302 | 4/2011 |
| WO | 2015/134837 A2 | 9/2015 |
| WO | WO-2017050849 A1 * | 3/2017 ............. A61K 31/18 |

OTHER PUBLICATIONS

Hounjet, Judith, et al. "The anti-malarial drug chloroquine sensitizes oncogenic NOTCH1 driven human T-ALL to γ-secretase inhibition." Oncogene 38.27 (2019): 5457-5468. (Year: 2019).*
U.S. Appl. No. 17/347,212 filed Nov. 12, 19, Inventor: Schirano.
Buono R., et al. "Fasting Mimicking Diet promotes immunotherapy-associated changes and inhibits auphagy to promote cancer free survival in Acute Lymphoblastic Leukemia models," The J. of Immunology, v. 204 (Supplement—May 1, 2020), 6 pgs.
International Search Report and Written Opinion dated May 2, 2022 for PCT Appn. No. PCT/US2021/061359, 26 pgs.
Lu, Z et al., "Fasting Selectively Blocks Development of Acute Lymphoblastic Leukemia via Leptin-Receptor Upregulation," Nature Medicine (2017), v. 23, n. 1, 14 pgs.
Search Rpt & Written Opinion dtd Aug. 9, 24 for EP Appn. No. 21901365.3, 8 pgs.

* cited by examiner

*Primary Examiner* — Bethany P Barham
*Assistant Examiner* — Peter Anthopolos
(74) *Attorney, Agent, or Firm* — Brooks Kushman P.C.

(57) ABSTRACT

A method for treating leukemia and in particular, lymphoblastic leukemia is provided. The method includes a step of administering an FMD to a subject identified as having leukemia optionally in combination with a chemotherapeutic agent and/or an autophagy inhibitor.

25 Claims, 34 Drawing Sheets

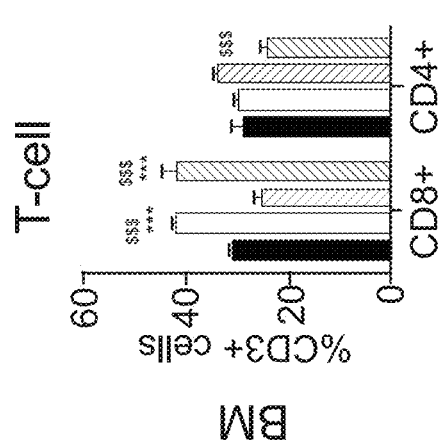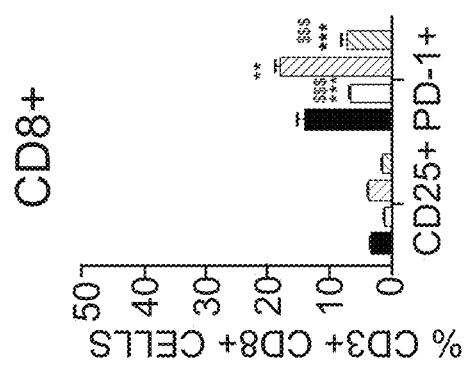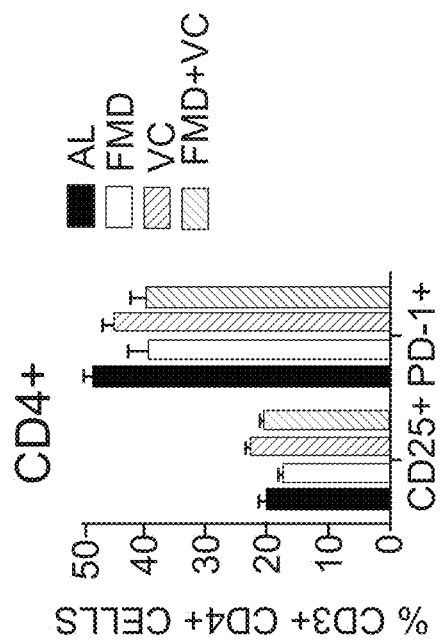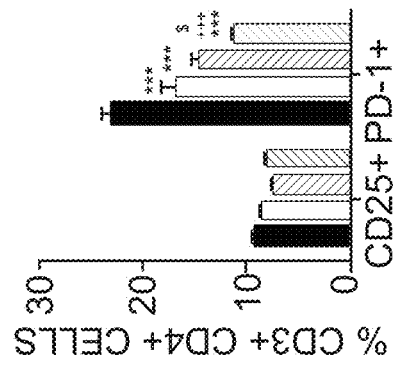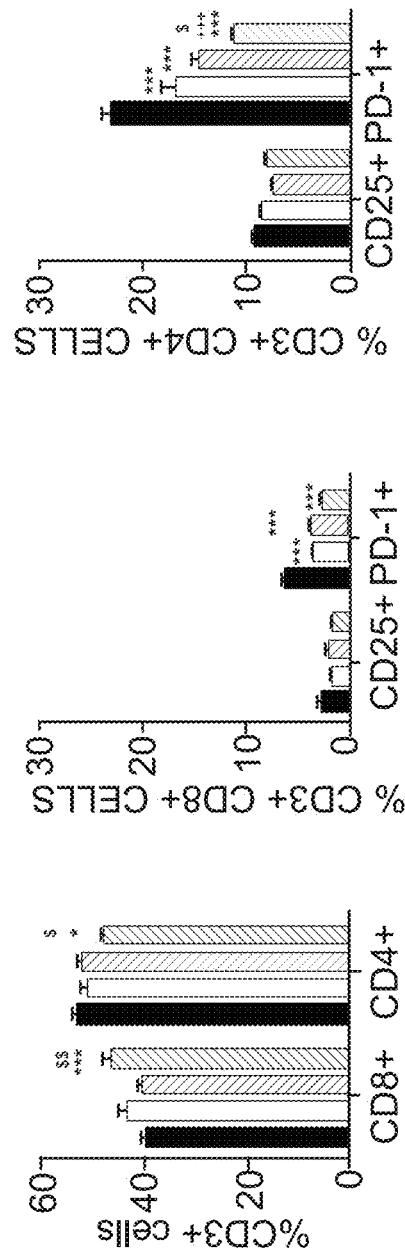

FASTING-MIMICKING DIET PROMOTES CANCER-FREE SURVIVAL IN ACUTE LYMPHOBLASTIC LEUKEMIA MODELS

CROSS-REFERENCE TO RELATED APPLICATIONS

This application claims the benefit of U.S. provisional application Ser. No. 63/119,922 filed Dec. 1, 2020, the disclosure of which is hereby incorporated in its entirety by reference herein.

STATEMENT REGARDING FEDERALLY SPONSORED RESEARCH OR DEVELOPMENT

The invention was made with Government support under Contract No. AG034906 awarded by the National Institutes of Health (NIH). The Government has certain rights to the invention.

TECHNICAL FIELD

In at least one aspect, the present invention is related to dietary compositions and methods for treating leukemia cancer, and in particular for treating lymphoblastic leukemia. In other aspects, the present invention promotes cancer free survival and it can also be used to enhance and to change the standard of care and to open the possibility to new clinical trial.

BACKGROUND

Pre-B cell acute lymphoblastic leukemia (ALL) is the most common childhood cancer but can also occur in older adults. It is a hematologic malignancy characterized by impaired differentiation and aggressive proliferation of clonal lymphoblasts in the bone marrow, spleen and blood[1]. The standard of care for B-ALL is chemotherapy, which includes vincristine, cyclophosphamide, anthracycline (daunorubicin or doxorubicin), or corticosteroids (prednisone or dexamethasone), and L-asparaginase[2]. The overall cure rate is about 80% in children but only 50% in adults for whom the relapse occurrence is high due to drug resistance[1,3]. There is still no consensus regarding the best treatment approach for newly diagnosed adults, and especially older patients.

It has previously been demonstrated that periodic fasting or Fasting Mimicking Diets (FMDs) reduce chemotherapy side effects, improve cancer treatment efficacy, and can also be effective by itself in delaying cancer progression in mice[4-13].

Accordingly, there is a need for improved methods for treating adults diagnosed with acute lymphoblastic leukemia.

SUMMARY

In at least one aspect, a method for treating leukemia is provided. The method includes a step of administering a fasting-mimicking diet to a subject identified as having leukemia.

In another aspect, a method for treating leukemia is provided. The method includes a step of administering a ketogenic FMD to a subject identified as having leukemia in combination with a chemotherapeutic agent and/or an autophagy inhibitor.

In another aspect, a fasting-mimicking diet package for treating leukemia is provided. The fasting-mimicking diet package includes breakfast, lunch, and dinner meal portions for administering a fasting-mimicking diet for each day of a first time period.

In another aspect, the use of the fasting-mimicking diet package described herein for forming a medicament for treating leukemia is provided.

In another aspect, the use of the fasting-mimicking diet package described herein for treating leukemia is provided.

In still another aspect, a method for preparing a fasting-mimicking diet package for treating a subject having leukemia. The method includes a step of receiving subject information for a subject having leukemia that includes a subject's weight. Meal portions are formed for each day of a predetermined time period during which a fasting-mimicking diet is administered, the meal portions providing a subject with from 30 to 50 percent of a subject's normal calorie consumption with protein and sugar rejection.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements and wherein:

FIGS. 2A-1, 2A-2, 2B-1, 2B-2, 2C, 2D-1, 2D-2, 2E, 2F, 2G-1, 2G-2, 2G-3, 2H, 2I-1, 2I-2, 2I-3, 2I-4, 2I-5, and 2I-6. Effects of STS in combination with vincristine on the mouse and human ALL cell lines. 2A-1 and 2A-2) cell count; 2B-1 and 2B-2) the LDH release of mouse and human ALL tumor cells; 2C) FACS analyses of AnnexinV and eFluor780 viability dye of mouse and H-ALL tumor cell line; 2D-1 and 2D-2) percentage data quantification of cells in early, late apoptosis and necrosis; 2E) provides a heatmap displaying autophagy gene expression in spleen tissue from AL, FMD, AL+VC and FMD+VC mouse (n=6/each group); 2F) protein analyses of LC3B, beclin1, p62 and vinculin in mouse spleen extract (n=6/group); 2G-1, 2G-2, and 2G-3) protein quantification performed by densitometric analysis using ImageJ64 software; H) protein analyses of LC3B, beclin1, p62 and tubulin with or without chloroquine (CQ) 100 μM in mouse and H-ALL cell line; and 2I-1 to 2I-6) relative protein quantification performed by densitometric analysis using ImageJ64 software.

FIGS. 3A, 3B, 3C, 3D-1, 3D-2, 3E-1, 3E-2, and 3E-3. Effect of FMD in combination with vincristine and chloroquine in an in vivo model of ALL. 3A) the experimental scheme; 3B) a survival curve of periodical FMD and vincristine in ALL in vivo model; 3C) spleen weight for each of the groups in FIGS. 3B; 3D-1 and 3D-2) quantification for GFP$^+$ tumor cells in bone marrow and spleen by FACS analyses: 3E-1, 3E-2, and 3E-3) relative quantifications of LC3B, beclin1, p62 and vinculin in mouse spleen extract performed by densitometric analysis using ImageJ64 software.

FIGS. 4A-1, 4A-2, 4B-1, 4B-2, 4C-1, 4C-2, 4D, 4E-1, 4E-2, 4E-3, and 4E-4. In vitro effects of STS in combination with vincristine on autophagy and apoptosis pathway. 4A-1 and 4A-2) evaluation of LDH release to assess cell viability and cytotoxicity in mouse and human ALL cell lines: 4B-1 and 4B-2) evaluation of LDH release to assess cell viability and cytotoxicity in mouse and human ALL cell lines after transfection with ULK1 siRNA (30 pM) or ATG9a (30 pM) siRNA with or without VC; 4C-1 and 4C-2 provide cell count of H-ALL tumor cells were cultured in STS or in CTRL medium after 48 h transfection with ULK1 siRNA (30 pM) or ATG9a (30 pM) siRNA+/−VC 5 nM; 4D) protein analyses of ULK1, ATG9a, and tubulin after 48 h of transfection with the specific siRNA (Si) in the normal medium; 4E-1 to 4E-4) western blot analyses; and 4E1 to 4E4) relative protein quantification of phosphorylated p53, cleaved caspase 3 and tubulin in M-ALL and H-ALL cells.

FIGS. 5A, 5B-1, 5B-2, 5B-3, 5B-4, 5B-5, 5B-6, 5B-7, 5B-8, 5B-9, 5C, 5D, and 5E. Effects of FMD in combination with vincristine on immune response. 5A) experimental scheme of one cycle of FMD and vincristine in ALL in vivo model (n=24); 5B-1 to 5B-9 provide FACS analyses quantification for CD3+CD4+, CD3+CD8+, CD3+CD4+PD-1+, CD3+CD4+CD25+, CD3+CD8+PD-1+ and CD3+CD8+CD25+ in bone marrow, spleen and blood. FIG. 5C provides the experimental scheme; 5D) survival curve of periodical FMD and VC in ALL in CD8+ in vivo depletion model; and 5E) FACS plots for CD3+CD4+ and CD3+CD8+ and histograms for GFP+ cancer cells in the bone marrow.

FIGS. 6A-1, 6A-2, 6A-3, 6A-4, 6A-5, 6B, 6C-1, 6C-2, 6D-1, 6D-2, 6D-3, 6D-4, and 6D-5. Effects of FMD in combination with vincristine on the immune response. 6A-1 to 6A-5) boxplot of T and B cell receptor repertoires in spleen tissue from AL, FMD, AL+VC and FMD+VC mouse (n=6/each group); 6B) visualization of molecular signature from AL, FMD, AL+VC and FMD+VC spleen (n=6/each group) using SaVanT software; 6C-1 and 6C-2 provides heatmaps displaying Th1 and Th2 cells gene expression in spleen tissue from AL, FMD, AL+VC and FMD+VC mouse (n=6/each group); and 6D-1 to 6D-5) Log 2 Fold Change of Pdcd-1, IL2ra, IL-10, CTLA-4, CD28 versus AL mice.

DETAILED DESCRIPTION

Figure 1A:
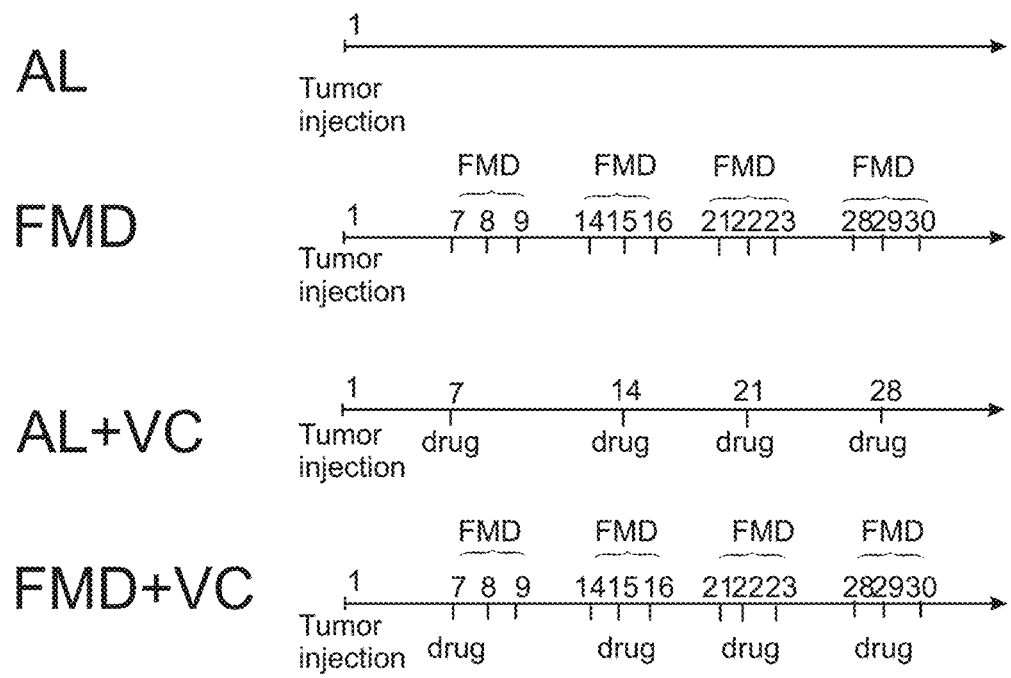
FIGS. 1A, 1B, 1C, 1D, 1E, 1F, 1G-1, and 1G-2. Effect of fasting mimic diet (FMD) in combination with vincristine in and in vivo model of ALL. 1A) experimental scheme; 1B) provides body weight (grams); 1C) survival curves of periodical FMD and vincristine in ALL in vivo model; 1D) a representative spleen picture; 1E) spleen weight (gr); 1F) GFP$^+$ RNA expression data; 1G-1 and 1G-2) FACS analyses quantification for GFP$^+$ tumor cells in bone marrow and spleen.

Reference will now be made in detail to presently preferred embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits.

Throughout this application, where publications are referenced, the disclosures of these publications in their entireties are hereby incorporated by reference into this application to more fully describe the state of the art to which this invention pertains.

The term "subject" refers to a human or other animal, including birds and fish as well as all mammals such as primates (particularly higher primates), horses, birds, fish sheep, dogs, rodents, guinea pigs, pig, cat, rabbits, and cows.

It should be appreciated that ranges for calories and nutritional components can be adjusted in accordance for a subject weight. For example, the endpoints of the ranges can be decreased for very light subjection and upward for obese subjects. In particular, these ranges can be adjusted by multiplying the endpoints by the subject's weight in pounds divided by 180 pounds (i.e., [(subject's weight in pounds)/180 lb.] or [(midpoint of a weight range in pounds)/180 lbs.]) optionally truncated to two or three significant figures. Such ranges includes ranges defined by the terms "at most," "at least", "less than," "greater than," and the like. Nutritional components includes any types of fat, protein, sugar, and carbohydrates as well as food components (e.g., carrots, beans, etc.).

Abbreviations:

"ALL" means acute lymphoblastic leukemia.

"AL" means Ad libitum.

"FMD" is fasting-mimicking diet.

"H-ALL" means human ALL.

"kcal" means kilocalorie.

"STS" means short time starvation.

"VC" means vincristine.

The terms "kilocalorie" (kcal) and "Calorie" refer to the food calorie. The term "calorie" refers to the so-called small calorie.

The term "subject" refers to a human or animal, including all mammals such as primates (particularly higher primates), sheep, dog, rodents (e.g., mouse or rat), guinea pig, goat, pig, cat, rabbit, and cow.

The term "normal caloric intake" means the number of kcal that a subject consumes to maintain his/her weight. In a refinement, a subject's normal caloric intake can be determined by interrogation or from the subject's weight. In another refinement, a subject's normal caloric intake is estimated from the formula:

$$\text{normal caloric intake} = \frac{2000 \text{ kcal}}{180 \text{ lb}} \times (\text{subject's weight in pounds})$$

which is estimated at 2000 kcal for a 180 pound subject.

The term "fasting mimicking diet" (FMD) means a diet that mimics the effects of fasting typically by providing a subject with at most 50% of their normal caloric intake but with some nutritional component so that fasting is mimicked while a subject is not completely starved. Typically, this diet is ketogenic since it causes an increase in ketone bodies and stimulates ketone body-based metabolism so it can also be referred to as a ketogenic FMD. In particular, FMD affects IGF-1, AKT and TOR signaling by regulation of growth hormone signaling upstream of IGF-1. It also affects the levels of glucose, the release of insulin, and the levels of the hunger hormone leptin. Low levels of IGF-1, leptin, insulin, and glucose and higher levels of ketone bodies and igfbp1 cooperate to promote the effects of the FMD. Examples of useful fasting mimicking and enhancing diets and methods for monitoring the effects of these diets on markers such as IGF-1 and IGFBP1 in the context of the present invention are set forth in U.S. patent application Ser. No. 14/273,946 filed May 9, 2014; Ser. No. 14/497,752 filed Sep. 26, 2014; Ser. No. 12/910,508 filed Oct. 22, 2010; Ser. No. 13/643,673 filed Oct. 26, 2012; Ser. No. 13/982,307 filed Jul. 29, 2013; Ser. No. 14/060,494 filed Oct. 22, 2013; Ser. No. 14/178,953 filed Feb. 12, 2014; Ser. No. 14/320,996 filed Jul. 1, 2014; Ser. No. 14/671,622 filed Mar. 27, 2015; the entire disclosure of these patent applications is hereby incorporated by reference. The fasting mimicking diet set forth in U.S. patent application Ser. Nos. 14/060,494 and 14/178,953 are found to be particularly useful in the present invention. Additional examples of FMD diets are found in U.S. patent application Ser. No. 15/148,251 and WIPO Pub. No. WO2011/050302 and WIPO Pub. No. WO2011/050302; the entire disclosures of which are hereby incorporated by reference. In a refinement, the FMD can be a low sodium diet that provides less than 1000 mg of sodium chloride per day.

In an embodiment, a method for treating leukemia, and in particular, lymphoblastic leukemia (e.g., acute lymphoblastic leukemia) is provided. The method includes a step of administering an FMD to a subject (e.g., a human subject) identified as having leukemia, and in particular, lymphoblastic leukemia. The fasting-mimicking diet is formulated to provide at most 50% of their normal caloric intake but with a nutritional component so that the subject is not starved. Such subjects are typically identified by blood tests and bone marrow biopsy. In a refinement, the FMD provides at most the following number of kcal:

$$\text{maximum FMD caloric intake} = \frac{2000 \text{ kcal}}{180 \text{ lb}} \times (\text{subject's weight in pounds}) \times 0.5.$$

In a variation, the FMD can be administered for a first time period of 1, 2, 3, 4, 5, 6, 7, 8, 9, or 10 days. Typically, the FMD is administered on consecutive days.

In a variation, the fasting-mimicking diet is administered in combination with a chemotherapeutic agent and/or an autophagy inhibitor, the chemotherapeutic agent and/or the autophagy inhibitor being administered during the administration of the fasting-mimicking diet. For example, for a chemotherapeutic agent and/or the autophagy inhibitor treatment, the FMD can be administered for 3 days, beginning 1 day before the chemotherapeutic agent and/or the autophagy inhibitor treatment. However, this protocol can be adjusted for chemotherapeutic agents and/or the autophagy inhibitor treatment that are more than once a month. For example, when the chemotherapeutic agent and/or the autophagy inhibitor treatments are administered once a week, the FMD can be administered for 3 days, beginning 1 day before the chemotherapeutic agent and/or the autophagy inhibitor treatment. When the chemotherapeutic agent and/or the autophagy inhibitor treatments are administered once a week, the FMD can be administered for 4 days, beginning 2 days before the chemotherapeutic agent and/or the autophagy inhibitor treatment.

Successful treatment is not particularly, limited by the specific chemotherapeutic agent and/or an autophagy inhibitor. Representative examples of chemotherapeutic agents include but are not limited to, vincristine, cyclophosphamide, anthracycline (daunorubicin or doxorubicin), or corticosteroids (prednisone or dexamethasone), and L-asparaginase, and combination thereof. Examples of autophagy inhibitors include but are not limited to chloroquine and hydroxychloroquine. Examples of corticosteroids include but are not limited to, hydrocortisone, hydrocortisone acetate, cortisone acetate, tixocortol pivalate, prednisolone, methylprednisolone, prednisone, amcinonide, budesonide, desonide, fluocinolone acetonide, fluocinonide, halcinonide, and triamcinolone acetonide, beclometasone, betamethasone, dexamethasone, fluocortolone, halometasone, and mometasone, alclometasone dipropionate, betamethasone dipropionate, betamethasone valerate, clobetasol propionate, clobetasone butyrate, fluprednidene acetate, and mometasone furoate, ciclesonide, cortisone acetate, hydrocortisone aceponate, hydrocortisone acetate, hydrocortisone buteprate, hydrocortisone butyrate, hydrocortisone valerate, prednicarbate, tixocortol pivalate, and combinations thereof.

Advantageously, the FMD, when administered to a subject diagnosed with leukemia, can delay cancer spread and growth and prolong survival when the FMD is administered with or without the chemotherapeutic agent and/or an autophagy inhibitor.

The human FMD includes ingredients, which are Generally Regarded As Safe (RGAS). An example of an FMD is manufactured for and commercialized by L-Nutra. This particular FMD package is available for purchase in the form of 5-days diet boxes, containing everything necessary for 5 days of the diet. Typically, the FMD includes lyophilized vegetable soups, bars, olives, crackers, herbal teas, supplements of vitamins and minerals, as set forth below in more detail.

In general, the FMD is formulated to provide 500 to 1250 kcal on the days that the FMD is administered. In a variation, the FMD is formulated to provide 800 to 1250 kcal on day 1 and 500 to 950 kcal on days 2, 3, 4, 5, or any additional days. In a refinement, the FMD is formulated to provide at most 1800 kcal, 1500 kcal, 1400 kcal, 1300 kcal, and 1250 kcal on day 1. In a further refinement, the FMD is formulated to provide at least 300 kcal, 400 kcal, 500 kcal, 600 kcal, and 800 kcal on day 1. Similarly, for days 2, 3, 4, 5, or any additional days, the FMD is formulated to provide at most 1500 kcal, 1400 kcal, 1300 kcal, 1250 kcal, 1000 kcal, and 950 kcal for each of days 2, 3, 4, 5, or any additional days. In another refinement, the FMD is formulated to provide at least 200 kcal, 300 kcal, 400 kcal, 500 kcal, and 600 kcal or each of days 2, 3, 4, 5, or any additional days. In a refinement, the FMD is formulated to provide 2.4 to 7 kcal per day for each day of the FMD, less than or equal to 30 g of sugar (e.g., 1 to 30 g) for each day of the FMD, less than 30 g of proteins (e.g., 1 to 30 g) for each day of the FMD, 15-30 grams of monounsaturated fats for each day of the FMD, 2-10 g of polyunsaturated fats for each day of the FMD, and less than 12 g of saturated fats (e.g., 1 to 12) for each day of the FMD.

Table 1 provides average values for calories, fast, total carbohydrates, sugar and protein for an example of the FMD. In a variation, the FMD provides for day 1 fat calories in an amount from about 40 to 80% of the total calories provided for day 1. For days 2, 3, 4, 5, and any additional day, the FMD provides fat calories in an amount from about 30 to 60% of the total calories provided for these days. In a refinement, the FMD provides for day 1 fat calories in an amount from about 50 to 70% of the total calories provided for day 1. For days 2, 3, 4, 5, and any additional day, the FMD provides fat calories in an amount from about 35 to 55% of the total calories provided for these days. In another refinement, the FMD provides for day 1 fat calories in an amount from about 55 to 65% of the total calories provided for day 1. For days 2, 3, 4, 5, and any additional day, the FMD provides fat calories in an amount from about 40 to 50% of the total calories provided for these days. Typically, the amount of carbohydrates on day 1 is greater than the amounts provided for days 2, 3, 4, 5, and any additional days. In a variation, the FMD provides for day 1, total carbohydrate calories in an amount from about 20 to 50% of the total calories provided for day 1. For days 2, 3, 4, 5, and any additional days, the FMD provides total carbohydrate calories in an amount from about 30 to 60% of the total calories provided for these days. In a refinement, the FMD provides for day 1, total carbohydrate calories in an amount from about 25 to 45% of the total calories provided for day 1. For days 2, 3, 4, 5, and any additional days, the FMD provides total carbohydrate calorie in an amount from about 35 to 50% of the total calories provided for these days. In a refinement, the FMD provides for day 1, total carbohydrate calories in an amount from about 30 to 40% of the total calories provided for day 1. For days 2, 3, 4, 5, and any additional days, the FMD provides total carbohydrate calorie in an amount from about 40 to 50% of the total calories provided for these days. Typically, the amount of carbohydrates on day 1 is less than the amounts provided for days 2, 3, 4, 5, and any additional days.

In a variation, the FMD provides for days 1, 2, 3, 4, 5, and any additional days, sugar calories in an amount from about 1 to 18% of the total calories provided for these days. In a refinement, the FMD provides for days 1, 2, 3, 4, 5, and any additional days, sugar calories in an amount from about 7 to 15% of the total calories provided for these days. In a refinement, the FMD provides for days 1, 2, 3, 4, 5, and any additional days, sugar calories in an amount from about 9 to 13% of the total calories provided for these days. In a variation, the FMD provides for days 1, 2, 3, 4, 5, and any additional days, protein calories in an amount from about 1 to 18% of the total calories provided for these day. In a refinement, the FMD provides for days 1, 2, 3, 4, 5, and any additional days, protein calories in an amount from about 7 to 15% of the total calories provided for these days. In a refinement, the FMD provides for days 1, 2, 3, 4, 5, and any additional days, protein calories in an amount from about 9 to 13% of the total calories provided for these days.

TABLE 1

The macronutrient content for each day of the 5 day FMD.

|  | Day 1 | Day 2, 3, 4, 5 and any additional days* |
|---|---|---|
| Total Calorie | 1.066 | ~746 |
| Fat | 59% | ~45% |
| Carbohydrate | 33% | ~46% |
| Sugar | 11% | ~10% |
| Protein | 9% | ~9% |

*Average values

In one variation of the FMD, for day 1, total calorie consumption is 3.5-5 kcal per pound (or 7.7-11 kcal per kilogram). The daily diet, to be fasting-mimicking and ketogenic, should contain less than or equal to 25 g of sugar (e.g., 1 to 25 g), less than 23 g of proteins (e.g., 1 to 23 g), 16-25 grams of monounsaturated fats, 4.8-8 g of polyunsaturated fats, and 1-10 g of saturated fats. For days 2, 3, 4, 5, or any additional days, total calorie consumption is 2.4-4 kcal per pound (or 5.3-8.8 kcal per kilogram). For days 2, 3, 4, 5, or any additional days, the diet should contain less than 16 g of sugars (e.g., 1 to 16 g of sugars), less than 15 g of protein (e.g., 1 to 15 g of protein), 8-12 g of monounsaturated fats, 2-4 g of polyunsaturated fats and 1-6 grams of saturated fats. Diet should also be high nourishment containing 100% of the RDA for vitamins, minerals, and essential fatty acids.

In another variation, the fasting-mimicking diet provides the subject with 4.5 to 7 kcal/pound of body weight/day on day 1 followed by 3 to 5 kcal/pound of body weight/day for days 2, 3, 4, 5, or any additional days. In a refinement, the fasting-mimicking diet provides the subject with 7 kcal/pound of body weight/day on day 1 followed by 4 kcal/pound of body weight/day for days 2, 3, 4, 5, or any additional days. In another variation, the fasting-mimicking diet provides the subject with 3-6 kcal/pound of body weight/day on day 1 followed by 2-4 kcal/pound of body weight/day for days 2-4.

In another variation, the FMD is formulated to provide less than 30 g of sugar on day 1 and less than 20 g of sugar on days 2, 3, 4, 5, or any additional days. The diet should contain less than 28 g of proteins on day 1 and less than 18 g of proteins on days 2, 3, 4, 5, or any additional days., mostly or completely from plant-based sources. The diet should contain between 20 and 30 grams of monounsaturated fats on day 1 and 10-15 grams of monounsaturated fats on days 2, 3, 4, 5, or any additional days. The diet should contain between 6 and 10 grams of polyunsaturated fats on day 1 and 3-5 grams of polyunsaturated fats on days 2, 3, 4, 5, or any additional days. The diet should contain less than 12 g of saturated fats on day 1 and less than 6 grams of saturated fats on days 2, 3, 4, 5, or any additional days.

Typically, the fats on all days are derived from a combination of the following: almonds, macadamia nuts, pecans, coconut, coconut oil, olive oil, and flaxseed. In a refinement, the FMD diet includes over 50% of the recommended daily value of dietary fiber on all days. In a further refinement, the amount of dietary fiber is greater than 15 grams per day on all five days or any additional days. The diet should contain 12-25 grams of glycerol per day on days 2, 3, 4, 5, or any additional days. In a refinement, glycerol is provided at 0.1 grams per pound body weight/day.

In some variations, the FMDs set forth herein are formulated to provide at least 60% calories from fatty acids and/or 2-5% calories from glycerol and/or up-to 5% of calories from plant-based proteins, and/or a maximum of 60% of calories from carbohydrates (these amounts are with respect to the total calories provided by the FMD. In some refinements, the FMD is formulated to provide a maximum of, in increasing order of preference, 15%, 12%, 10%, 8%, 6%, or 5% calories from plant-based proteins. In some refinements, the FMD is formulated to provide a maximum, in increasing order of preference, 65%, 60%, 55%, 50%, 60%, 35% calories from carbohydrates of the total calories provided by the FMD. Advantageously, carbohydrates are complex carbohydrates from plant sources such as soy, rice, or other grains. It should be appreciated that typically the amount of plant-based proteins and carbohydrates are greater than 1% of the total calories provided by the FMD At least a portion of the fats on all days are derived from a combination of the following: almonds, macadamia nuts, pecans, coconut, coconut oil, olive oil and flaxseed. In a refinement, at least 50% of the calories from fatty acids are from coconut oil and tree nuts (e.g., macadamia nuts, walnuts, or almonds). Additional fat sources include vegetable oil such as soybean oil. In a further refinement, the low protein diet incudes fat sources such that at least 25 percent of calories from fat are short-chain fatty acids having from 2 to 7 carbon atoms and/or from medium-chain saturated fatty acids having from 8 to 12 carbon atoms. Specific examples of fatty acids include lauric and/or myristic acid, and fat sources include olive oil, kernel oil and/or coconut oil. In another refinement, the fasting-mimicking diet includes calories from fat in an amount from about 0 to 22 percent of the total calories contained in the diet.

Advantageously, the FMD diet can be formulated to provide over 50% of the recommended daily value of dietary fiber on all days. In a refinement, the amount of dietary fiber is greater than 15 grams per day on all five days or any additional days. In some variations, the fasting-mimicking diet includes 2 to 5% calories from glycerol. The FMD can be formulated to provide 12-25 grams of glycerol per day on days 2, 3, 4, 5, or any additional days. In a refinement, glycerol is provided at 0.1 grams per pound body weight (of the subject)/day.

In some variations, the FMDs set forth herein are formulated to provide the following micronutrients (at least 95% non-animal based): over 5,000 IU of vitamin A per day (days 1-5 or any additional days.); 60-240 mg of vitamin C per day (days 1-5 or any additional days); 400-800 mg of Calcium per day (days 1-5 or any additional days); 7.2-14.4 mg of Iron per day (days 1-5 or any additional days); 200-400 mg of Magnesium per day (days 1-5 or any additional days); 1-2 mg of copper per day (days 1-5 or any additional days); 1-2 mg of Manganese per day (days 1-5 or any additional days); 3.5-7 mcg of selenium per day (days 1-5 or any additional days); 2-4 mg of Vitamin B1 per day (days 1-5 or any additional days); 2-4 mg of Vitamin B2 per day (days 1-5 or any additional days); 20-30 mg of Vitamin B3 per day (days 1-5 or any additional days); 1-1.5 mg of Vitamin B5 per day (days 1-5 or any additional days); 2-4 mg of Vitamin B6 per day (days 1-5 or any additional days); 240-480 mcg of Vitamin B9 per day (days 1-5 or any additional days); 600-1000 IU of Vitamin D per day (days 1-5 or any additional days); 14-30 mg of Vitamin E per day (days 1-5 or any additional days); over 80 mcg of Vitamin K per day (days 1-5 or any additional days); 16-25 mcg Vitamin B12 are provided during the entire 5-day period or any additional days; 600 mg of Docosahexaenoic acid (DHA, algae-derived) are provided during the entire 5-day period or any additional days. The FMD diet provides high micronutrient content mostly (i.e., greater than 50 percent by weight) from natural sources including: Kale, Cashews, Yellow Bell Pepper, Onion, Lemon Juice, Yeast, Turmeric. Mushroom, Carrot, Olive Oil, Beet Juice, Spinach, Tomato, Collard, Nettle, Thyme, Salt, Pepper, Vitamin B12 (Cyanocobalamin), Beets, Butternut Squash, Oregano, Tomato Juice, Orange Juice, Celery, Romaine Lettuce, Cumin, Orange Rind, Citric Acid, Nutmeg, Cloves, and combinations thereof. These micronutrients can be provided in the FMD as a micronutrient supplement composition. The micronutrient supplement composition in these meal plans is a vegetable powder with vitamins and minerals supplements. Table 2 provides an example of additional micronutrient supplementation that can be provided in the FMD diet.

TABLE 2

Micronutrient Supplementation

| | Supplement | Formula | Amount | Amount Range | Unit |
|---|---|---|---|---|---|
| Vitamin A | | | 1250 1U | 900-1600 | IU |
| Vitamin C | Ascorbic Acid | $C_6H_8O_6$ | 15.0000 | 10-20 | mg |
| Ca | Calcium Carbonate | $CaCO_3$ | 80.0000 | 60-100 | mg |
| Fe | Ferrous Fumarate | $C_4H_2FeO_4$ | 4.5000 | 3-6 | mg |
| Vitamin D3 | Cholecalciferol | $C_{27}H_{44}O$ | 0.0025 | 0.001-0.005 | mg |
| Vitamin E | dl-Alpha Tocopheryl Acetate | $C_{29}H_{50}O_2$ | 5.0000 | 3-7 | mg |
| Vitamin K | Phytonadione | | 0.0200 | 0.1-0.04 | mg |
| Vitamin B1 | Thiamine Mononitrate | $C_{12}H_{17}N_5O_4S$ | 0.3750 | 0.15-0.5 | mg |
| Vitamin B2 | Riboflavin E101 | $C_{17}H_{20}N_4O_6$ | 0.4250 | 0.2-0.6 | mg |
| Vitamin B3 | Niacinamide | $C_6H_6N_2O$ | 5.0000 | 3-7 | mg |
| Vitamin B5 | Calcium Pantothenate | $C_{18}H_{32}CaN_2O_{10}$ | 2.5000 | 1.5-4.0 | mg |

TABLE 2-continued

Micronutrient Supplementation

| | Supplement | Formula | Amount | Amount Range | Unit |
|---|---|---|---|---|---|
| Vitamin B6 | Pyridoxine Hydrochloride | $C_8H_{11}NO_3 \cdot HCl$ | 0.5000 | 0.3-0.7 | mg |
| Vitamin B7 | Biotin | $C_{10}H_{16}N_2O_3S$ | 0.0150 | 0.01-0.02 | mg |
| Vitamin B9 | Folic Acid | $C_{19}H_{19}N_7O_6$ | 0.1000 | 0.07-0.14 | mg |
| Vitamin B12 | Cyanocobalamin | $C_{63}H_{88}CoN_{14}O_{14}P$ | 0.0015 | 0.001-0.002 | mg |
| Cr | Chromium Picolinate | Cr(C6H4NO2)3 | 0.0174 | 0.014-0.022 | mg |
| Cu | Cupric Sulfate | $CuSO_4$ | 0.2500 | 0.18-0.32 | mg |
| I | Potassium Iodide | KI | 0.0375 | 0.03-0.045 | mg |
| Mg | Magnesium Oxide | MgO | 26.0000 | 20-32 | mg |
| Mn | Manganese Sulfate | $MnSO_4$ | 0.5000 | 0.3-0.7 | mg |
| Mo | Sodium Molybdate | $Na_2MoO_4$ | 0.0188 | 0.014-0.023 | mg |
| Se | Sodium Selenate | $Na_2O_4Se$ | 0.0175 | 0.014-0.023 | mg |
| Zn | Zinc Oxide | ZnO | 3.7500 | 3-5 | mg |

It should be appreciated, that the FMD can be formulated to within plus/minus 20 percent of the values indicated in Table 2.

In some variations, the FMD includes caloric restriction with respect to proteins and sugars (e.g., glucose). In one refinement, the fasting-mimicking diet includes protein in an amount that is less than 15 percent of total calories provided by the fasting-mimicking diet. In a further refinement, the fasting-mimicking diet includes protein in an amount that is at most, in increasing order of preference, 15%, 12%, 10%, 8%, or 5% of total calories provided by the fasting-mimicking diet and in an amount that is at least 0%, 2%, 3%, 5%, or 6% of total calories provided by the fasting-mimicking diet. In another refinement, the fasting-mimicking diet includes sugars in an amount that is less than 15 percent of the total calories provided by the fasting-mimicking diet. In a further refinement, the fasting-mimicking diet includes sugars (e.g., glucose) in an amount that is at most, in increasing order of preference, 15%, 12%, 10%, 8%, or 5% of total calories provided by the fasting-mimicking diet and in an amount that is at least, in order of preference, 0%, 2%, 3%, 5%, or 6% of total calories provided by the fasting-mimicking diet.

An example of a useful FMD package is provided in U.S. Pat Pub No. 20180228198; the entire disclosure of which is hereby incorporated by reference. Such FMDs can include soups, nutrition bars, crackers (e.g., kale crackers), an optional energy drink with a glucose substitute, olives, vitamin and mineral supplements (e.g., with a vegetable powder), algal oil, and optional teas. The FMD can include nutrition bars, and soups are meals to be consumed for breakfast, lunch, and dinner. Examples of soup compositions are disclosed in U.S. Pat Pub No. 20180228198; the entire disclosure of which is hereby incorporated by reference. Examples of nutrition bars are disclosed in U.S. Pat Pub No. 20180228198; U.S. patent application Ser. No. 16/680,911 filed Nov. 12, 2019; and U.S. Pat. No. 17,347,212, filed Jun. 14, 2021 the entire disclosures of which are hereby incorporated by reference. Examples of nutrition bars are disclosed in U.S. Pat Pub No. 20180228198; and U.S. Pat. No. 17,347,212, filed Jun. 14, 2021 the entire disclosures of which are hereby incorporated by reference. It should be appreciated that each of the soup, broth, tea, and energy drink compositions set forth herein can be in powder or solid form and are designed to have added water when consumed.

Typically, the FMD provides one or more FMD soups on each day of the diet. Each FMD soup can be formulated to provide less than about 1 gram of saturated fat per serving, less than about 5 grams of trans fat per serving (optimally, less than 1 gram of trans fat), less than about 10 grams of protein per serving, less than about 40 grams of carbohydrates per serving.

In a variation, each FMD soup is formulated to provide from about 80 kcal to 150 kcal preserving. In the context of formulations, "provide" also means "includes." In a refinement, each FMD soup is formulated to provide about 1 to 5 grams of total fat per serving. In a further refinement, each FMD soup is formulated to provide less than about 1 grams of saturated fat per serving and less than about 5 grams of trans fat (optimally, less than 1 gram of trans fat). In a refinement, each FMD soup is formulated to provide less than about 10 grams of protein per serving. In a further refinement, each FMD soup is formulated to provide from about 1 to 8 grams of protein per serving. In a further refinement, each FMD soup is formulated to provide from about 2 to 6 grams of protein per serving. In still another refinement, each FMD soup is formulated to provide less than about 40 grams of carbohydrates per serving. In a further refinement, each FMD soup is formulated to provide from about 10 to 35 grams of carbohydrates per serving. In still another refinement, each FMD soup is formulated to provide from about 20 to 30 grams of carbohydrates per serving.

The FMD soups can be formulated with in these limits from any combination of components selected from the group consisting of black beans, butternut squash, *quinoa*, tomatoes, mushrooms, white beans (e.g., great northern beans), brown beans, spinach, green tea extract, rice flour, onions, brown rice powder, carrots, inulin, leeks, olive oil, cabbage, potatoes, olives, peas, pumpkin, maltodextrin, and celery, chicory root fiber, sea salt, yeast, basil, parsley, garlic, rosemary extract, coriander, oregano, potato starch, potato flakes, zucchini squash, turmeric. In a refinement, the FMD soup can be formulated with in these limits from a first component selected from the group consisting of black beans, butternut squash, *quinoa*, tomatoes, mushrooms, white beans (e.g., great northern beans), brown beans, spinach, and combinations thereof and a second component selected from the group consisting of green tea extract, rice flour, onions, brown rice powder, carrots, inulin, leeks, olive oil, cabbage, potatoes, olives, peas, pumpkin, maltodextrin, and celery, chicory root fiber, sea salt, yeast, basil, parsley, garlic, rosemary extract, coriander, oregano, potato starch, potato flakes, zucchini squash, turmeric, and combinations thereof. Typically, the FMD soups are provided as a powder that can be combined with water to form the soup, typically, with heating.

Examples of soups includes vegetable soups, *quinoa*-containing minestrone soups, mushroom-containing soup, tomato-containing soup composition, bean-containing minestrone soup composition, pumpkin soup composition, white bean and spinach soup, back bean soup, butternut squash soup, butternut squash and *quinoa* soup, and a vegetable broth. A specific example of a vegetable soup composition includes onions, tomatoes, spinach, green tree extract, optionally rice flour, optionally brown rice powder, optionally carrots, leeks, and optionally inulin. A specific example of a *quinoa*-containing minestrone soup composition includes *quinoa*, green tea extract, optionally olive oil, optionally cabbage, optionally potatoes, optionally rice flour, and optionally tomatoes and optionally no turmeric. A specific example of a vegetable soup composition includes carrots, inulin, leeks, onions and rice flour. A specific example of a mushroom-containing soup composition includes mushrooms, green tea extract, optionally brown rice powder, optionally carrots, and optionally inulin. A specific example of a mushroom-containing soup composition includes carrots, inulin, mushrooms, onions, and rice flour. A specific example of a tomato-containing soup composition includes tomatoes, green tea extract, optionally inulin, and optionally onions. A specific example of a tomato-containing soup composition includes tomatoes, inulin, olives, onions, potatoes, and rice flour. A specific example of a *quinoa*-containing minestrone soup composition includes *quinoa*, green tea extract, optionally olive oil, optionally cabbage, optionally potatoes, optionally rice flour, and optionally tomatoes and optionally no turmeric. A specific example of a *quinoa*-containing minestrone soup composition includes *quinoa*, green tea extract, optionally olive oil, optionally cabbage, optionally potatoes, optionally rice flour, and optionally tomatoes and optionally no turmeric. A specific example of a bean-containing minestrone soup composition includes white beans (e.g., great northern beans), great tea extract, optionally cabbage, and optionally potatoes. In a refinement, the bean-containing minestrone soup composition includes brown beans, carrots, peas, potato, and rice flour. A specific example of a pumpkin soup composition includes pumpkin, green tree extract, optionally rice flour, optionally carrots, and optionally brown rice powder. A specific example of a first vegetable broth includes carrots, maltodextrin, celery, spinach, and tomatoes. A specific example of a vegetable broth includes carrots, maltodextrin, celery, spinach, and tomatoes. A specific example of a white bean and spinach soup composition includes white beans, whole grain brown rice, rice flour, chicory root fiber, olive oil, spinach leaves, sea salt, celery, onion, yeast extract, and garlic. A specific example of a black bean soup composition includes black beans, chicory root fiber, whole grain brown rice, olive oil, potato starch, rosemary extract, sea salt, onion, yeast extract, garlic, coriander, and oregano. A specific example of a butternut squash composition includes butternut squash, rice flour, whole grain brown rice, chicory root fiber, sea salt, carrots, olive oil, potato starch, rosemary extract, onion, and yeast extract. A specific example of a butternut squash and *quinoa* composition includes butternut squash, *quinoa*, whole grain brown rice, rice flour, chicory root fiber, olive oil, potato starch, rosemary extract, sea salt, onion, yeast extract, garlic, and chives.

In a variation, a first FMD nutrition bar is formulated to provide from about 150 kcal to 350 kcal per serving. In a refinement, the first FMD nutrition bar is formulated to provide about 10 to 35 grams of total fat per serving. In a further refinement, the first FMD nutrition bar is formulated to provide less than about 8 grams of saturated fat per serving and optionally, less than about 5 grams of trans fat (optimally, less than 1 gram of trans fat). In a refinement, each FMD nutrition bar is formulated to provide less than about 10 grams of protein per serving. In a further refinement, the first FMD nutrition bar is formulated to provide from about 1 to 8 grams of protein per serving. In a further refinement, the first FMD nutrition bar is formulated to provide from about 2 to 6 grams of protein per serving. In still another refinement, the first FMD nutrition bar is formulated to provide less than about 30 grams of carbohydrates per serving. In a further refinement, the first FMD nutrition bar is formulated to provide from about 8 to 25 grams of carbohydrates per serving. In still another refinement, the first FMD nutrition bar is formulated to provide from about 10 to 18 grams of carbohydrates per serving. The first FMD nutrition bar can be formulated within these limits with any combination of macadamia nuts, honey, pecans, almonds, almond butter, coconut flour, sea salt, mixed tocopherols (vitamin E), citric acid, and ascorbic acid.

In a variation, a second FMD nutrition bar is formulated to provide from about 70 kcal to 120 kcal per serving. In a refinement, the second FMD nutrition bar is formulated to provide about 3 to 10 grams of total fat per serving. In a further refinement, the second FMD nutrition bar is formulated to provide less than about 5 grams of saturated fat per serving and optionally, less than about 5 grams of trans fat (optimally, less than 1 gram of trans fat). In a refinement, each FMD nutrition bar is formulated to provide less than about 6 grams of protein per serving. In a further refinement, the second FMD nutrition bar is formulated to provide from about 1 to 6 grams of protein per serving. In a further refinement, the second FMD nutrition bar is formulated to provide from about 2 to 5 grams of protein per serving. In still another refinement, the second FMD nutrition bar is formulated to provide less than about 20 grams of carbohydrates per serving. In a further refinement, the second FMD nutrition bar is formulated to provide from about 5 to 18 grams of carbohydrates per serving. In still another refinement, the second FMD nutrition bar is formulated to provide from about 10 to 15 grams of carbohydrates per serving. The second FMD nutrition bar can be formulated within these limits with any combination of inulin, almond butter, brown rice crispy, cocoa powder, almonds, chocolate chips (cane sugar, unsweetened chocolate, cocoa butter), rolled oats, brown rice syrup, flaxseed oil, rice dextrin, grape juice, and salt.

In a refinement, the energy drink composition includes glycerin preferably in an amount of 20 to 60 weight %; water (purified) preferably in an amount of 40 to 80 weight %.

In another refinement, the drink powder composition includes total fat in an amount that provides from about 300 to about 700 kcal per 100 grams of the drink powder or ready to drink composition; carbohydrates in an amount that provides from about 50 to 150 kcal per 100 grams of the drink powder or ready to drink composition; and proteins in an amount that provides from about 30 to about 60 kcal per 100 grams of the drink powder composition or ready to drink composition.

In another embodiment, a fasting drink is provided. The fasting drink is typically formed from a fasting drink powder composition which is dissolved in water. In a refinement, the fasting drink and/or the fasting drink powder composition includes total fat in an amount that provides from about 200 to about 600 kcal per 100 grams of the fasting drink and/or the fasting drink powder composition; saturated fat in an amount from about 40 to 70 kcal per 100 grams of the fasting drink and/or the fasting drink powder composition; carbohydrates in an amount that provides from about 100 to 200 kcal per 100 grams of the fasting drink and/or the fasting drink powder composition; and proteins in an amount that provides from about 30 to about 60 kcal per 100 grams of the fasting drink and/or the fasting drink powder composition.

In another variation, the fasting drink and/or the fasting drink powder composition includes fat in an amount of at least, in increasing order of preference, 30 weight percent, 40 weight percent, 45 weight percent, or 50 weight percent and fat in an amount of at most, in increasing order of preference, 70 weight percent, 65 weight percent, 60 weight percent, or 55 weight percent. In a refinement, the fasting drink and/or the fasting drink powder composition includes saturated fat in an amount of at least, in increasing order of preference, 8 weight percent, 5 weight percent, 2 weight percent, or 1 weight percent and saturated fat in an amount of at most, in increasing order of preference, 20 weight percent, 15 weight percent, 10 weight percent, or 8 weight percent. The fasting drink and/or the fasting drink powder composition also includes carbohydrates in an amount of at least, in increasing order of preference, 1 weight percent, 3 weight percent, 10 weight percent, 15 weight percent, 20 weight percent, or 25 weight percent and carbohydrates in an amount of at most, in increasing order of preference, 35 weight percent, 30 weight percent, 40 weight percent, 38 weight percent, 35 weight percent, or 30 weight percent. The fasting drink and/or the fasting drink powder composition also includes proteins in an amount of at least, in increasing order of preference, 1 weight percent, 2 weight percent, 3 weight percent, 5 weight percent, or 8 weight percent and protein in an amount of at most, in increasing order of preference, 20 weight percent, 18 weight percent, 17 weight percent, 16 weight percent, or 15 weight percent. Unless stated to the contrary all percentages are weight percentages of the total weight of the fasting drink and/or the fasting drink powder composition. The fats used for the fasting drink and/or the fasting drink powder composition includes midchain triglycerides and/or monosaturated fat and/or and polyunsaturated fat. Suitable sources of monosaturated fat, but are not limited to, peanut butter, olives, nuts (e.g., almonds, pecans, pistachios, cashews), avocado, seeds (e.g., sesame), oils (e.g., olive, sesame, peanut, canola), etc. Suitable sources of polyunsaturated fat include, but are not limited to, walnuts, seeds (e.g., pumpkin, sunflower), flaxseed, and oils (e.g., safflower, soybean, corn).

In a refinement, the second vegetable broth (chicken flavoring) includes carrots, chicken flavoring, maltodextrin, celery, spinach, soy lecithin, and tomatoes. In a refinement, the second vegetable broth composition includes carrot (dehydrated, puffed, powder, pieces) preferably in an amount of 3 to 10 weight %; celery preferably in an amount of 3 to 12 weight %; garlic preferably in an amount of 3 to 9 weight %; maltodextrin preferably in an amount of 8 to 25 weight %; oil (canola) preferably in an amount of 0.5 to 2 weight %; onion preferably in an amount of powder, minced) preferably in an amount of 3 to 12 weight %; parsley preferably in an amount of 3 to 10 weight %; potato preferably in an amount of 1 to 6 weight %; salt preferably in an amount of 8 to 25 weight %; soy lecithin preferably in an amount of 0.5 to 3 weight %; spinach (leaf, powder) preferably in an amount of 3 to 12 weight %; tomatoes (fruit powder, sun dried, granules) preferably in an amount of 6 to 18 weight %; xanthan gum preferably in an amount of 0.5 to 4 weight %; and yeast extract preferably in an amount of 4 to 12 weight %.

In a refinement, the energy drink composition includes glycerin preferably in an amount of 20 to 60 weight %; water (purified) preferably in an amount of 40 to 80 weight %.

In a refinement, the tea composition that includes spearmint includes spearmint leaves organic preferably in an amount of 70 to 100 weight %.

In a refinement, the tea composition that includes lemon and spearmint includes lemon myrtle organic preferably in an amount of 3 to 12 weight %; lemon peel organic preferably in an amount of 10 to 25 weight %; spearmint leaves organic preferably in an amount of 50 to 95 weight %.

In a refinement, the tea composition that includes hibiscus includes hibiscus tea leaves organic preferably in an amount of 80 to 100 weight %.

In a refinement, the algal oil composition includes schizocatrium algae oil (DHA Omega-3) preferably in an amount of 80 to 100 weight %.

In a refinement, the nutrient replenishment composition (NR-1) includes beet root powder, calcium carbonate, carrots, collard leaf, kale leaf, and tomatoes. In a refinement, the nutrient replenishment composition (NR-1) includes ascorbic acid preferably in an amount of 1 to 3 weight %; beet root powder preferably in an amount of 6 to 20 weight %; beta carotene preferably in an amount of 0.05 to 0.15 weight %; calcium carbonate preferably in an amount of 6 to 20 weight %; carrot (dehydrated, puffed, powder, pieces) preferably in an amount of 6 to 20 weight %; cholecalciferol preferably in an amount of 0.00 weight %; chromium Picolinate preferably in an amount of 0.00 weight %; collard leaf powder preferably in an amount of 6 to 20 weight %; cupric sulfate preferably in an amount of 0.01 to 0.06 weight %; cyanocobalamin, 0.00; Dl-alpha tocopherol acetate preferably in an amount of 0.3 to 1 weight %; ferrous fumarate preferably in an amount of 0.2 to 1 weight %; folic acid preferably in an amount of 0.00 weight %; kale leaf preferably in an amount of 6 to 20 weight %; magnesium stearate preferably in an amount of 1 to 6 weight %; manganese sulfate preferably in an amount of 0.04 to 0.08 weight %; niacinamide preferably in an amount of 0.3 to 1 weight %; pantothenic acid preferably in an amount of 0.1 to 0.6 weight %; phytonadione preferably in an amount of 0.00 weight %; potassium iodine preferably in an amount of 0 weight %; pyridoxine HCl preferably in an amount of 0.03 to 0.1 weight %; riboflavin preferably in an amount of 0.02 to 0.1 weight %; sodium molybdate preferably in an amount of 0.00 weight %; sodium selenate preferably in an amount of 0.00 weight %; spinach (leaf, powder) preferably in an amount of 6 to 20 weight %; thiamine mononitrate preferably in an amount of 0.02 to 0.1 weight %; tomatoes (fruit powder, sun dried, granules) preferably in an amount of 6 to 20 weight %; tribasic calcium phosphate preferably in an amount of 0.5 to 2 weight %; and zinc oxide preferably in an amount of 0.2 to 0.8 weight %.

Table 3 provides an example of nutrient content for each day of the 5 day FMD regimen based on an average 180-200 lbs. person. It should be appreciated that practice within plus/minus 30 or 20 percent of the values indicated in Table 3 is contemplated, optionally truncated to 2 or 3 significant figures. Tables 4 and 5 provide exemplary meal plans for implementing the FMD.

TABLE 3

The nutrient content for each day of the 5 day FMD regimen based on an average 180-200 lbs. person.

|  | Unit | Day 1 | Day 2, 3, 4, 5 and any additional days* |
|---|---|---|---|
| Total Fat | (g) | 70 | 37.25 |
| % DV |  | 90 | 47.75 |
| Protein | (g) | 23 | 15 |
| % DV |  | 47 | 30.5 |
| Total Carbohydrate | (g) | 103 | 95.5 |
| % DV |  | 37 | 35 |
| Sugars | (g) | 28.84 | 17.74 |
| Dietary Fiber | (g) | 31 | 20 |
| % DV |  | 112 | 72.25 |
| VIT A | (IU) | 3.253 | 3.043 |
| % DV |  | 361 | 314.5 |
| VIT C | (mg) | 113 | 61.5 |
| % DV |  | 125 | 71 |
| Calcium | (mg) | 400 | 249.3 |
| % DV |  | 31 |  |
| Iron | (mg) | 12 | 7.25 |
| % DV |  | 64 | 40.25 |
| Sodium | (mg) | 2.126 | 24.5 |
| % DV |  | 92 | 75.75 |
| Potassium | (mg) | 1.127 | 830 |
| % DV |  | 24 | 15 |

% DV indicates the percent of daily value based on a 2.000 kcal diet updated to 2020 regulations.
*Average values

TABLE 4

Meal Plan Variety 1

|  | Day 1 | Day 2 | Day 3 | Day 4 | Day 5 |
|---|---|---|---|---|---|
| Breakfast | L-Bar Nut-based[1] Herbal Tea Algal Oil (2) | L-Bar Nut-based[1] Herbal Tea | L-Bar Nut-based[1] Herbal Tea | L-Bar Nut-based[1] Herbal Tea | L-Bar Nut-based[1] Herbal Tea Algal Oil |
| Lunch | Tomato Soup Mix NR-1[4] (2)[5] Crackers Olives | Mushroom Soup Mix NR-1[4] (1)[5] Olives | Tomato Soup Mix NR-1[4] (1)[5] Crackers | Vegetable Soup Mix NR-1[4](1)[5] Olives | Tomato Soup Mix NR-1[4] (1)[5] Crackers |
| Afternoon | Herbal Tea L-Bar Nut-based[1] | Herbal Tea Olives | Herbal Tea | Herbal Tea Olives | Herbal Tea |
| Dinner | Minestrone Soup Mix L-Bar Choco Crisp[2] | Minestrone with Quinoa Soup Mix L-Bar Choco Crisp[2] | Minestrone Soup Mix | Minestrone with Quinoa Soup Mix L-Bar Choco Crisp[2] | Minestrone Soup Mix |
| All over the day |  | L-Drink[3] | L-Drink[3] | L-Drink[3] | L-Drink[3] |

[1]An example of the first nutrition bar.
[2]An example of the second nutrition bar.
[3]Energy drink with glucose substitute
[4]Micronutrient supplement composition.
[5] Values in parenthesis are the number of doses.

TABLE 5

Meal Plan Variety 2

|  | Day 1 | Day 2 | Day 3 | Day 4 | Day 5 |
|---|---|---|---|---|---|
| Breakfast | L-Bar Nut-based[1] Herbal Tea Algal Oil (2) | L-Bar Nut-based[1] Herbal Tea | L-Bar Nut-based[1] Herbal Tea | L-Bar Nut-based[1] Herbal Tea | L-Bar Nut-based[1] Herbal Tea Algal Oil |
| Lunch | Butternut Squash Soup Mix NR-1[4] (2)[5] Crackers Olives | Tomato Soup Mix NR-1 (1)[5] Olives | Butternut Squash Soup Mix NR-1[4] (1)[5] Crackers | Tomato Soup Mix NR-1[4] (1)[5] Olives | White Bean and Spinach Soup Mix NR-1[4] (1)[5] Crackers |
| Afternoon | Herbal Tea L-Bar Nut-based[1] | Herbal Tea Olives | Herbal Tea | Herbal Tea Olives | Herbal Tea |
| Dinner | Black Bean Soup Mix L-Bar Choco Crisp[2] | Butternut Squash and Quinoa Soup Mix L-BarChoco Crisp[2] | White Bean and Spinach Soup Mix | Black Bean Soup Mix L-Bar Choco Crisp | Butternut Squash and Quinoa Soup Mix |
| All over the day |  | L-Drink[3] | L-Drink[3] | L-Drink[3] | L-Drink[3] |

[1]An example of the first nutrition bar.
[2]An example of the second nutrition bar.
[3]Energy drink with glucose substitute
[4]Micronutrient supplement composition.
[5] Values in parenthesis are the number of doses.

The micronutrient supplement composition in these meal plans is a vegetable powder with vitamins and minerals supplements. With respect to the 5 day meal plans, it should be appreciated that it the diet is administered for fewer days, the identified protocol for a given day is used. For example, for a 3 day FMD, days 1, 2, and 3 are used. Likewise, for a FMD that is administered for greater than 5 days, any of the daily protocols for days 2-5 can be used for these additional days.

In some variations, a refeeding diet is administered to the subject for a second time period after the first time period during which the FMD is administered. The refeeding diet provides an overall calorie consumption that is within 10 percent of a subject's normal calorie consumption. In this context, normal calorie consumption is the number of calories needed to maintain the subject's weight at their pre-treatment weight or to maintain a predetermined target weight. Therefore, the refeeding diet can be referred to as a "refeeding diet." Although the present invention is not significantly limited by the second time period, the second time period can be from 7 days to 6 months or longer. Typically, the second time period is from 5 days to 26 days or longer following the FMD. In some refinements, the refeeding diet provides at most, in increasing order of preference, 2500 kcal/day, 2400 kcal/day, 2300 kcal/day, 2200 kcal/day, 2100 kcal/day, 2000 kcal/day, 1900 kcal/day, 1800 kcal/day, 1700 kcal/day, 1600 kcal/day, or 1500 kcal/day. In some further refinements, the refeeding diet provides at least, in increasing order of preference, 1200 kcal/day, 1300 kcal/day, 1400 kcal/day, 1500 kcal/day, 1600 kcal/day, 1700 kcal/day, or 1800 kcal/day.

In a variation, the cycle of an FMD for a first time period and the refeeding diet for a second time period is repeated a plurality of times over a plurality of months or years. In a refinement, the cycle is repeated for 1 to 25 cycles.

In another embodiment, a fasting-mimicking diet (FMD) package for treating leukemia is provided. The fasting-mimicking diet package includes breakfast, lunch, and dinner meal portions for administering a fasting-mimicking diet for each day of a first time period. In particular, the fasting-mimicking diet package includes nutrition bars and soups to be consumed for breakfast, lunch, and dinner as set forth above. In a refinement, the fasting-mimicking diet is administered for a first time period of 1, 2, 3, 4, 5, 6, 7, 8, 9, or 10 days. Typically, these are consecutive days.

The fasting-mimicking diet package provides rations for implementing the fasting-mimicking diet. The FMD is formulated to provide 800 to 1250 kcal on day 1 and 500 to 950 kcal on days 2-5 or any additional days. In a variation, the fasting-mimicking diet package includes rations that provide 2.4 to 7 kcal per day for each day of the fasting-mimicking diet, less than or equal to 30 g of sugar for each day of the fasting-mimicking diet, less than 30 g of proteins for each day of the fasting-mimicking diet, 15-30 grams of monounsaturated fats for each day of the fasting-mimicking diet, 2-10 g of polyunsaturated fats for each day of the fasting-mimicking diet, and less than 12 g of saturated fats for each day of the fasting-mimicking diet.

In a variation, the fasting-mimicking diet package includes rations for day 1 that provide 3.5 to 5 kcal per pound of the subject. In a refinement, the fasting-mimicking diet package includes rations for day 1 that provide less than 25 g of sugar, less than 23 g of proteins, 16-25 grams of monounsaturated fats, 4.8 to 8 g of polyunsaturated fats, and 1 to 10 g of saturated fats. In this variation, the fasting-mimicking diet package includes rations for days 2 to 5 or any additional days, total calorie consumption that provides 2.4 to 4 kcal per pound of the subject for each day. In a refinement, the fasting-mimicking diet package includes rations days 2 to 5 or any additional days that provide less than 16 g of sugars, less than 15 g of protein, 8 to 12 g of monounsaturated fats, 2 to 4 g of polyunsaturated fats and 1 to 6 grams of saturated fats.

In another variation, the fasting-mimicking diet packages include rations for the soups, nutrition bars, crackers, an optional drink with a glucose substitute, olives, vitamin and mineral supplements, algal oil, and optional teas as set forth above. Therefore, the details of these components for the fasting-mimicking diet packages are the same as set forth above.

In another embodiment, a method for preparing the fasting-mimicking diet package set forth above is provided. The method includes a step of receiving subject information for a subject having leukemia that includes a subject's weight. In a refinement, the subject information includes the age, gender, and diagnosis (i.e., leukemia) of the subject. Meal portions are formed for each day of a predetermined time period during which a fasting-mimicking diet is administered. These meal portions can include a breakfast portion, a lunch portion, and a dinner portion. In a refinement, the meal portions further include snack portions and drink portions. Characteristically, the meal portions provide a subject with at most 50 percent of a subject's normal calorie consumption with protein and sugar rejection as set forth above. In a refinement, the diet package is assembled to provide from 30 to 50 percent of the average normal calorie consumption with protein and sugar rejection as set forth above. In a refinement, the normal caloric intake can be defined by the following formula:

$$\text{normal caloric intake} = \frac{2000 \text{ kcal}}{180 \text{ lb}} \times (\text{subject's weight in pounds}).$$

In another variation, subject information for a plurality of subjects having leukemia is received. The plurality of subjects can be grouped with predetermined weight ranges, each range having an average weight. Diet packages for each weight range are assembled based on the average weight for each weight range. For example, all subjects having a normal weight below 200 can be treated with the unscaled FMD while heavier subjects treated with a scaled version. In a refinement, the weight ranges can be incremented from a start weight with a predefined value (with each range including only the upper or lower endpoint). For example, the weight ranges can be 100-120 lbs., 100-120 lbs., 120-140 lbs., 140-160 lbs., 160-180 lbs., 180-200 lbs., 200-220 lbs., 220-240 lbs., 240-260 lbs. etc. Useful increments can be 5 lbs., 10 lbs., 15 lbs., 20 lbs., 25 lbs. etc. The diet packages are assembled to provide at most 50% of an average normal caloric intake for each weight range with protein and sugar restriction as set forth above. In a refinement, the diet packages are assembled to provide a from 30 to 50 percent of the average normal calorie consumption with protein and sugar restriction as set forth above. In a variation, the average normal caloric intake for a weight range is given by:

$$\text{average normal caloric intake} = \frac{2000 \text{ kcal}}{180 \text{ lb}} \times (\text{midpoint of a weight range}).$$

It should be appreciated that in these variations for preparing diet package(s), the ranges and amount for fat, carbohydrates, protein, sugars as well as the compositions for the soups, nutrition bars and other FMD components can be independently scaled with by a factor (e.g., subject's weight in pounds divided by 180 lbs. or midpoint of a weight range divided by 180 lbs.) that adjusts the amounts to compensate for a subject's weight. For example, the fasting-mimicking diet and the fasting-mimicking diet package that provides 2.4 to 7 kcal per day for each day of the fasting-mimicking diet, less than or equal to 30 g of sugar for each day of the fasting-mimicking diet, less than 30 g of proteins for each day of the fasting-mimicking diet, 15-30 grams of monounsaturated fats for each day of the fasting-mimicking diet, 2-10 g of polyunsaturated fats for each day of the fasting-mimicking diet, and less than 12 g of saturated fats for each day of the fasting-mimicking diet can be scaled with by a factor of subjects weight in pounds divided by 180 lbs.

It should also be appreciated that diet packages can be prefabricated before being requested or receiving the subject information. In this case, upon receiving the subject information or request for an order for a weight or weight range, the diet package is sent to a customer (e.g., consumer).

The following examples illustrate the various embodiments of the present invention. Those skilled in the art will recognize many variations that are within the spirit of the present invention and the scope of the claims.

The FMD has been developed to cause cancer cell death and effectively treat and/or cure leukemia. A 3-day regimen of FMD in combination with chemotherapy induces cancer-free survival in a syngeneic mouse model of BCR-ABL ALL leukemia by inhibition of autophagy and induction of cancer cell death. The results set forth below demonstrate that the combined treatment of FMD+VC+autophagy inhibitor chloroquine (CQ) leads to synergistic effects and high levels of cancer-free survival in mice. Furthermore, the combined treatment inhibits the immune resistance response and induces a strong immune-dependent attack of cancer cells in the spleen. Mice treated with FMD+VC have a higher presence of CD3+CD8+ cells and a reduction of CD3+CD4+ cells, together with a lower pool of PD-1+ T cells in bone marrow, spleen and blood. The combination of FMD+VC generates changes commonly associated with immunotherapy and is consistent with the role of the immune system in cancer-free survival. Further, the in vivo depletion of CD8+ cells reverses the effect of FMD+VC on cancer-free survival. Moreover, FMD+VC induces the expression of genes for a cancer immune response, including upregulation of CD28, and it decreases the expression of coinhibitory receptors (such as Pdcd-1), of regulatory gene IL2ra (CD25), of immunosuppressive cytokines (such as IL10) and displays a trend for a decrease in CTLA-4 in the tumor microenvironment. The present invention can be used to enhance and to change the standard of care for ALL leukemia and to open the possibility to new clinical trials for blood cancer In Vivo ALL Model:

50 mice C57BL/6J (20 weeks old) purchased from The Jackson Laboratory were injected via retro-orbital injection with $1 \times 10^4$ GFP-expressing BCR/ABL syngeneic leukemia cancer cells/mice. One week later the mice were divided into 4 groups: Ad lib+ vehicle (AL n=10), Fasting Mimicking Diet (FMD n=12) 4 cycles+vehicle, Ad lib+ chemo drugs (vincristine (AL+VC n=14), I.P. 0.5 mg/kg once a week and FMD+VC (n=14).

Mouse FMD Diet:

The mouse version of the FMD is a 3-day regimen. Mice on the FMD diet were fed 50% of the standard daily calorie intake on day 1 and 10% of normal daily calorie intake on days 2 to 3. All mice were supplied with fresh food during the morning hours (8 am-10 am). Post-FMD refeeding: after the end of the day 2-3 diet, mice were fed ad libitum regular chow for up to 4 days to regain body weight before the next FMD cycle.

CD8+ Cells In Vivo Depletion:

Complete depletion of CD8+ CTL was achieved by intraperitoneal administration of neutralizing monoclonal antibody (αCD8; clone YTS 169.4 BioXCell, Cat #BP0117) or rat IgG (BioXCell, Cat #BP0090) every 4 days after 1 week of tumor implantation. The depletion of circulating CD8+ CTL over time was confirmed by FACS analysis.

Cell Culture and Treatment:

BCR/ABL syngeneic leukemia cells ("8093 cells") were cultured at a density of $2.5 \times 10^5$ cells/mL in a standard condition McCoy's 5A media supplemented with 10% FBS, murine IL-3, beta-mercapto ethanol and gentamycin or in STS condition (0.5 g/liter of glucose; 2% FBS). Human leukemia cells H-ALL (BV173) were cultured in RPMI media supplemented with 10% FBS and gentamycin or in STS condition. Both mouse and human cell line were treated for 24 h or 48 h with or without vincristine (VC) 5 nM. Cell viability were measured by Mini Automated Cell Counter Moxi or by Trypan Blue exclusion dye.

For ULK1 and ATG9a silencing, cells were seeded at 60-80% of confluence, they were transfected for 48 h with 30 pM ULK1 and ATG9a siRNA (Life technologies ID:65268, 125425) using Lipofectamine RNAiMAx Reagent (ThermoFisher) according to manufacturer instructions.

LDH Assay:

Cell cytotoxicity were measured using the colorimetric CytoTox 96® Non-Radioactive Cytotoxicity Assay (Promega) following the manufacture instructions. The assay quantitatively measures lactate dehydrogenase (LDH), a stable cytosolic enzyme that is released in culture supernatants upon cell lysis. The amount of color formed is proportional to the number of lysed cells.

FACS Analyses:

Flow cytometry analyses of mouse BM and SP GFP+ leukemia cell were performed to assess the engraftment. Annexin V staining: The cells were staining with eFLuor 780 Fixable Viability Dye and PE-Cy7 Annexin V (eBioscience) according to the instructions of the manufacturer. Analysis was performed with BD FACS diva on LSR II.

Western Blotting:

Total cell lysates were prepared using the RIPA buffer (Thermo Scientific) according to manufacturer instructions. Protein concentration was measured with BCA assay (Thermo Scientific). Equal amounts of protein (30 µg) were heat-denaturized in lane marker reducing sample buffer (Thermo Scientific), resolved by SDS-PAGE using Novex 4-20% Tris-Glycine MiniProtein Gels (Thermo Scientific), and transferred to PVDF membranes (Millipore, Darmstadt, Germany). The filters were blocked in 5% BSA for 1 h at room temperature and then incubated O.N at 4° with primary antibody directed against cleaved caspase 3, phosphorylated p53, beclin1, p62, LC3B, ULK1, vinculin (Cell Signaling rabbit mAb #9664, rabbit mAb #9284, rabbit mAb #3495, rabbit mAb #5114, rabbit mAb #2775, rabbit mAb #8054, rabbit mAb #18799), ATG9 (GeneTex rabbit mAb #GTX128427), and tubulin (Millipore #05-661). Peroxidase conjugated IgG (Santa Cruz, CA, USA) was used as secondary antibody. Membrane-bound immune complexes were detected by ultra-sensitive enhanced chemiluminescence system (Thermo Scientific) on a photon-sensitive film (Hyperfilm ECL, GE Healthcare, Milano, Italy). Quantification was performed by densitometric analysis using ImageJ64 software.

RNA-Seq Library Preparation and Data Analysis:

Total RNA was extracted from the spleen using RNeasy Mini kit (QIAGEN) followed by on-column DNase I digestion as per the manufacturer's instructions. RNA integrity was verified with a Bioanalyzer (Agilent Technologies, Santa Clara, CA, USA). RNA was quantified with the Qubit fluorometer (Invitrogen), and 1 µg of purified RNA was utilized as starting material for library construction, which was carried out with the KAPA RNA HyperPrep Kit with RiboErase (KAPA BIOSYSTEM KK8560) as per manufacturer's instructions. Libraries were sequenced with an Illumina HiSeq 3000 system using 50-bp single-end reads. The RNA-Seq reads are mapped to the mouse GRCm38 references using HISAT2 (2.1.0) 55 with tuned parameters determined in (Baruzzo, G., et al. Simulation-based comprehensive benchmarking of RNA-seq aligners. Nat Methods 14, 135-139 (2017)). The script used to map reads is available at https://github.com/smangul1/recycle.RNA.seq/blob/master/benchmark_RNASeq_aligners/code/run.hisat2.tuned.sh. The resulting mapped reads of each sample are stored in a binary format file (.bam). Gene counts were obtained by counting the number of sequencing reads overlapping each of the genes (HTSeq v0.6.1). Gene annotations (ENSEMBL GRCh38, gtf format) were downloaded from www.ensembl.org. The script htseq-count is supplied with the GTF file with gene models and a bam file containing the mapped reads. The script generates individual gene counts by examining the read overlap with the genes. We choose a conservative setting (--mode=intersection-strict) to handle reads overlapping more than one feature. Thus, reads overlapping several genes simultaneously are marked as reads with no feature and excluded from consideration. Gene counts from every sample are used to determine genes differentially expressed across the conditions (DeSeq2 with default parameters). DeSeq2 models read counts as a negative binomial distribution and uses shrinkage estimation for dispersions and fold changes58. Within-group variability (variability between replicates) is used to determine if the observed difference between the conditions may be attributed to the experimental conditions and not to the biological variance. FDR corrected p-values are used to control the number of false positives.

TCR and IG clonotypes from unmapped reads and reads mapped to the TCR and IG loci were assembled using ImReP. ImReP is a two-stage alignment-free approach to assemble CDR3 sequences and detect corresponding V(D)J recombination. We have calculated the TCR/IG load as the total number of reads supporting assembled TCR/IG clonotypes.

Molecular signatures in gene expression profile were analyzed using Savant Software59 (http://newpathways.mcdb.ucla.edu/savant-dev/).

Statistics and Experimental Design:

All experiments were repeated at least three independent times. All samples represent biological replicates. Unless otherwise specified in figure legends, all center values shown in graphs refer to the mean. For statistical significance of the differences between the means of two groups, we used two-tailed Student's t-tests. Statistical significance of differences among multiple groups (≥3) was calculated by performing ANOVA multiple comparisons of the means for each group. The survival rates of the two groups were analyzed using a log-rank test and were considered to be statistically significant if P<0.05. No samples or animals were excluded from analysis, and sample size estimates were not used. Animals were randomly assigned to groups. Studies were not conducted blinded.

Figure 1B:
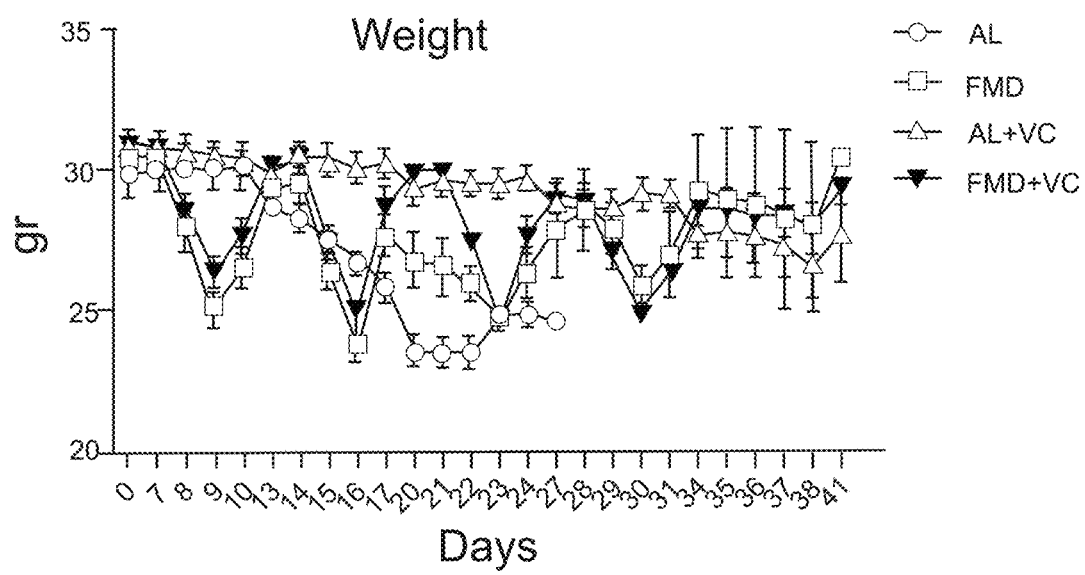
Figure 1C:
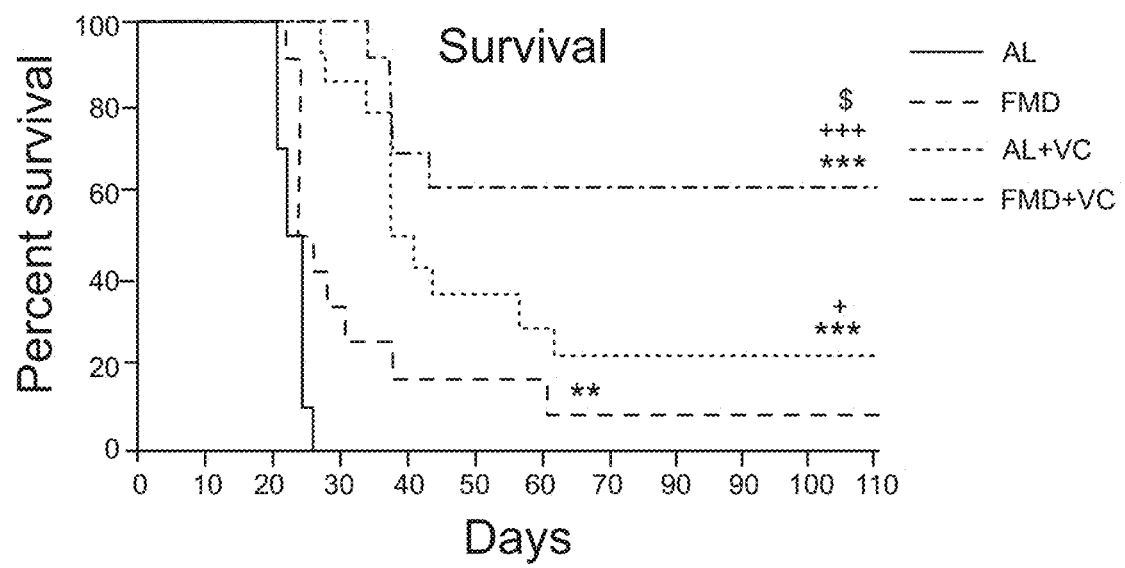
Figure 1D:
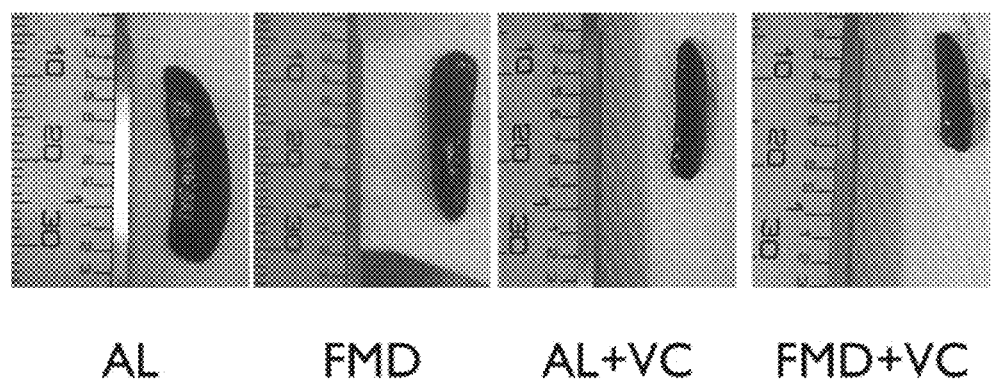
Figure 1E:
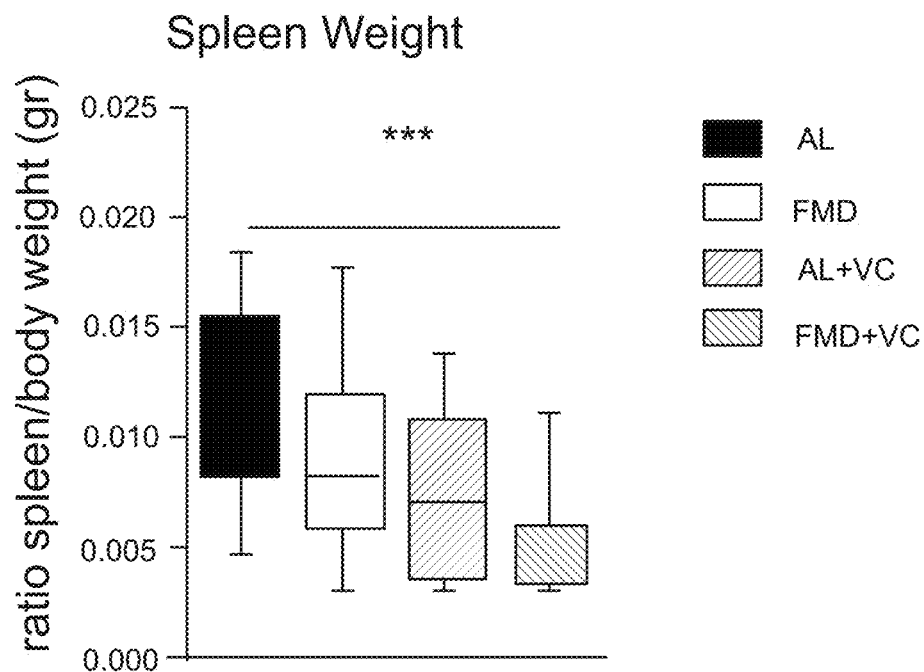
Figure 1F:
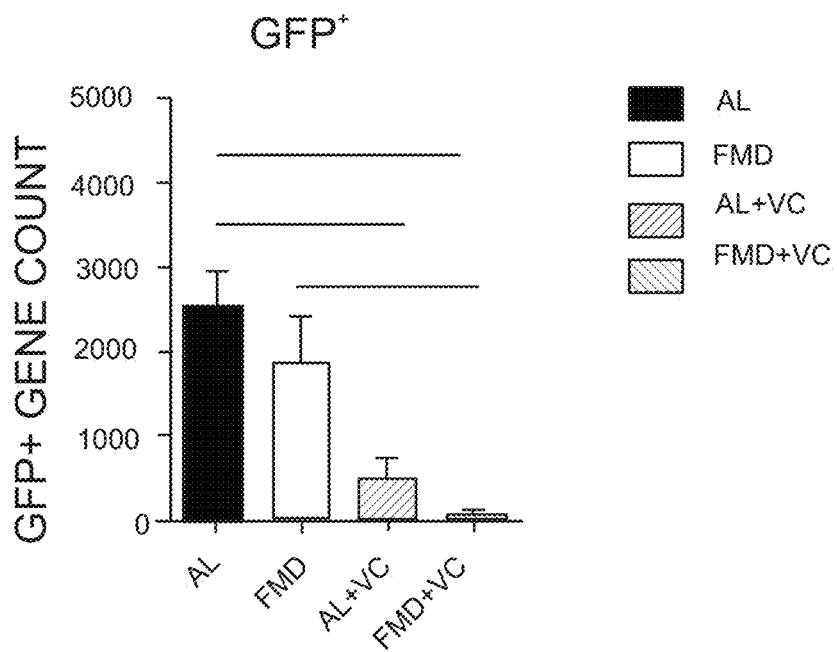
Figures 1, 1G:
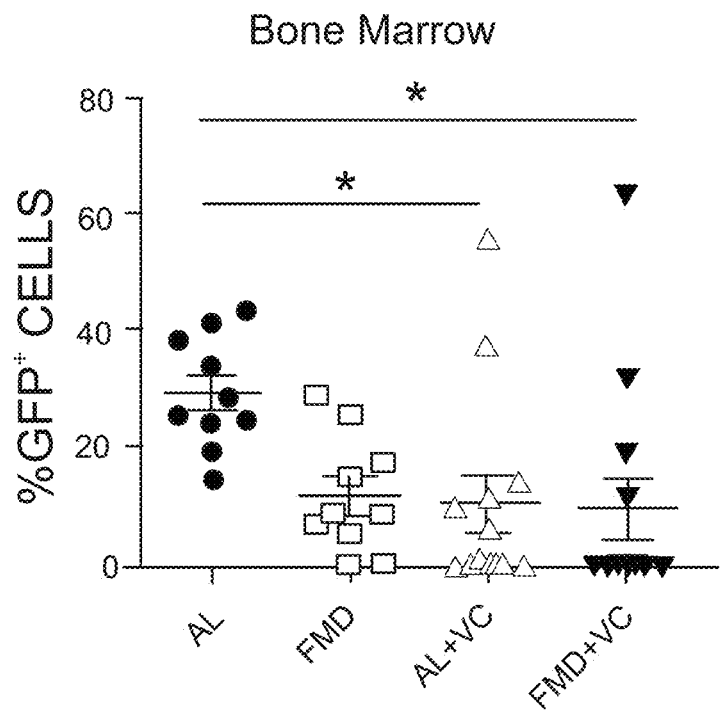
Figures 1, 1G, 2:
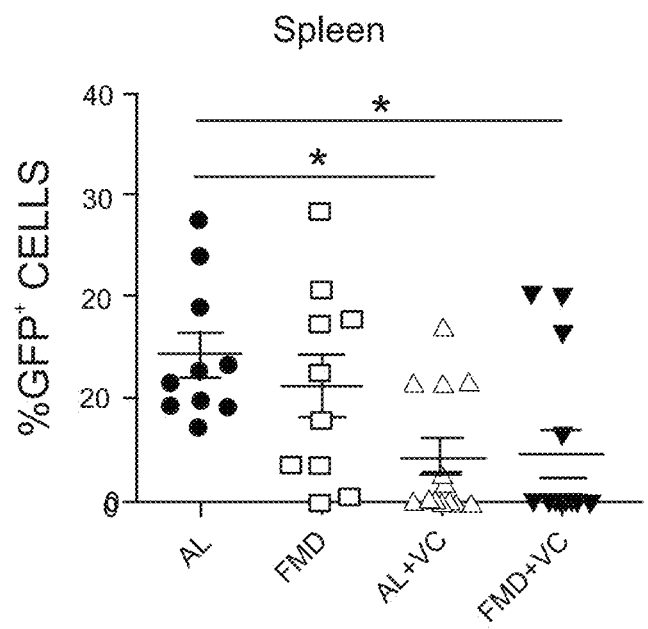

FIG. 1 shows the effect of fasting mimic diet (FMD) in combination with vincristine in in vivo model of ALL. FIG. 1A shows the experimental scheme. FIG. 1B provides body weight (gr) and FIG. 1C survival curves of periodical FMD and vincristine in ALL in vivo model. 50 mice C57BL/6J (20 weeks old) was injected via retro-orbital injection with $1 \times 10^4$ GFP-expressing BCR/ABL syngeneic leukemia cancer cells/mice. One week later the mice were divided into 4 groups: Ad lib+vehicle (AL n=10), Fasting Mimicking Diet (FMD n=12) 4 cycles+vehicle, Ad lib+ chemo drugs (vincristine (AL+VC n=14), I.P. 0.5 mg/kg once a week and FMD+VC (n=14). (p<0.01 , p<0.001 * vs AL: p<0.05+ p<0.01++vs FMD: p<0.05 $ vs AL+VC). FIG. 1D provides a representative spleen picture. FIG. 1E shows spleen weight (gr) and FIG. 1F shows GFP+ RNA expression data. FIGS. 1G-1 and 1G-2 show FACS analyses quantification for GFP+ tumor cells in bone marrow and spleen. Data are expressed as mean+/−s.e.m. *p<0.05, p<0.01, *p<0.001, one-way ANOVA.

Figures 1, 2A:
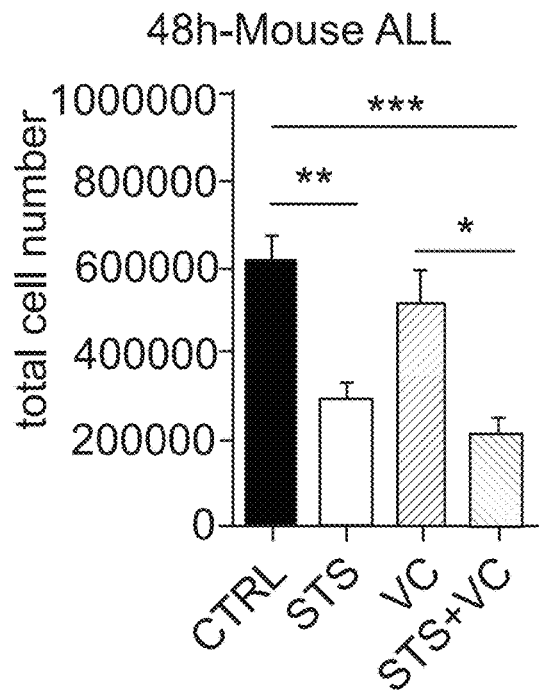
Figures 1, 2B:
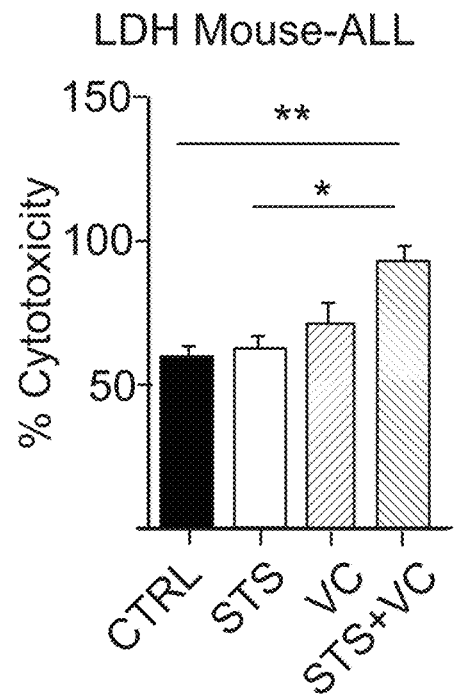
Figures 2, 2A:
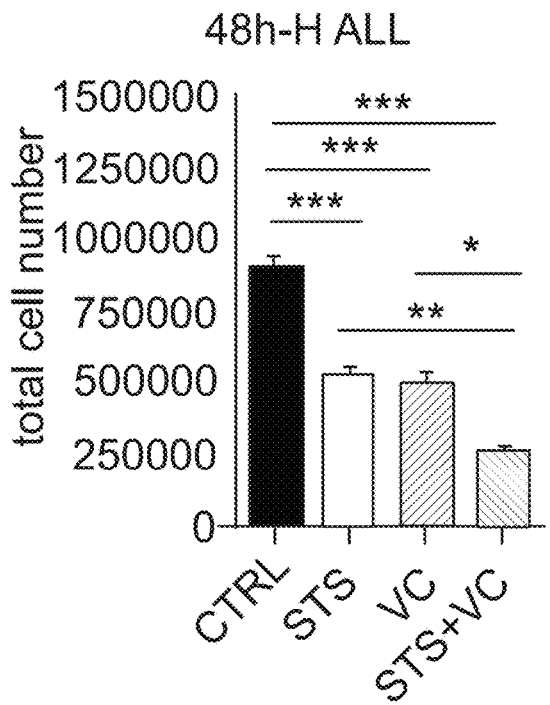
Figures 2, 2B:
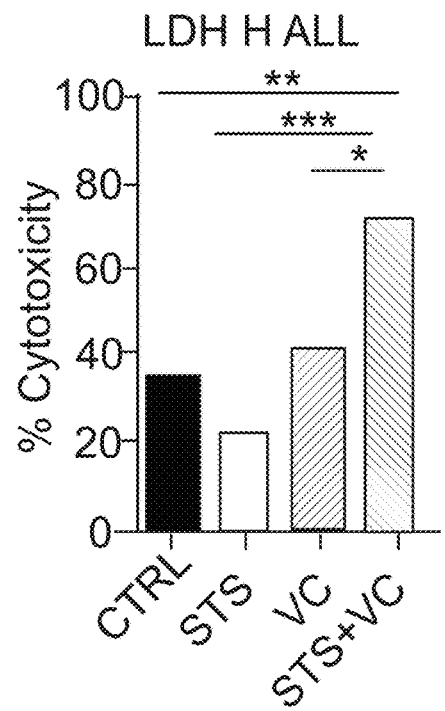
Figure 2C:
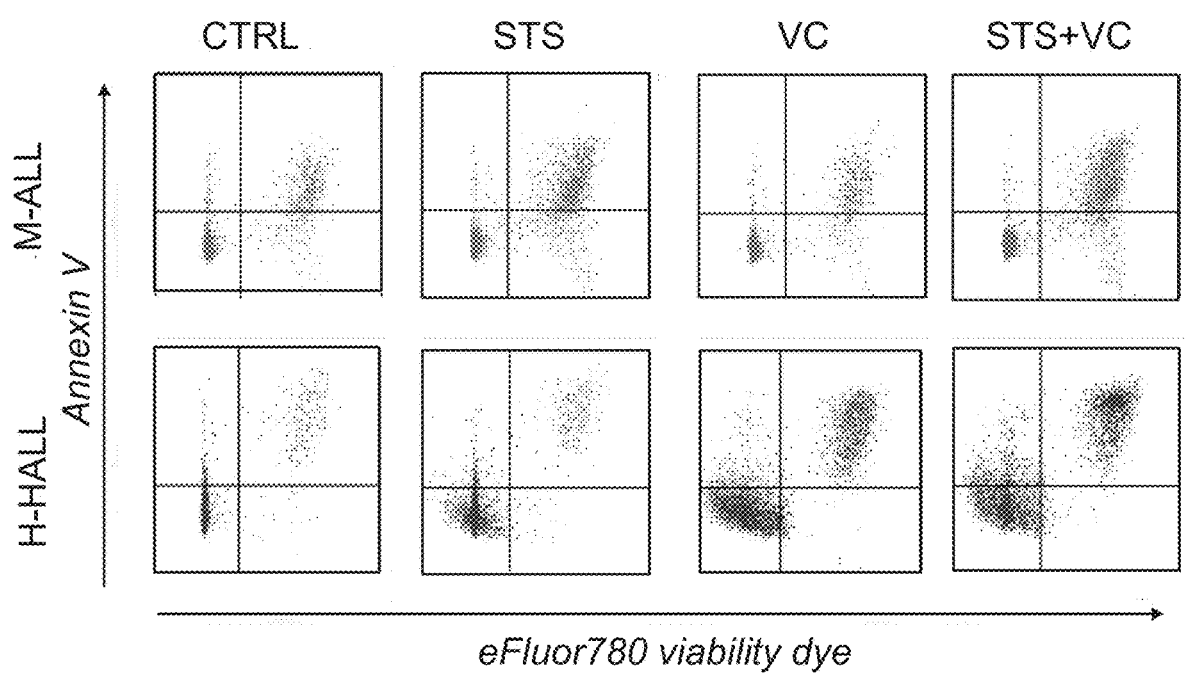
Figures 1, 2, 2D:
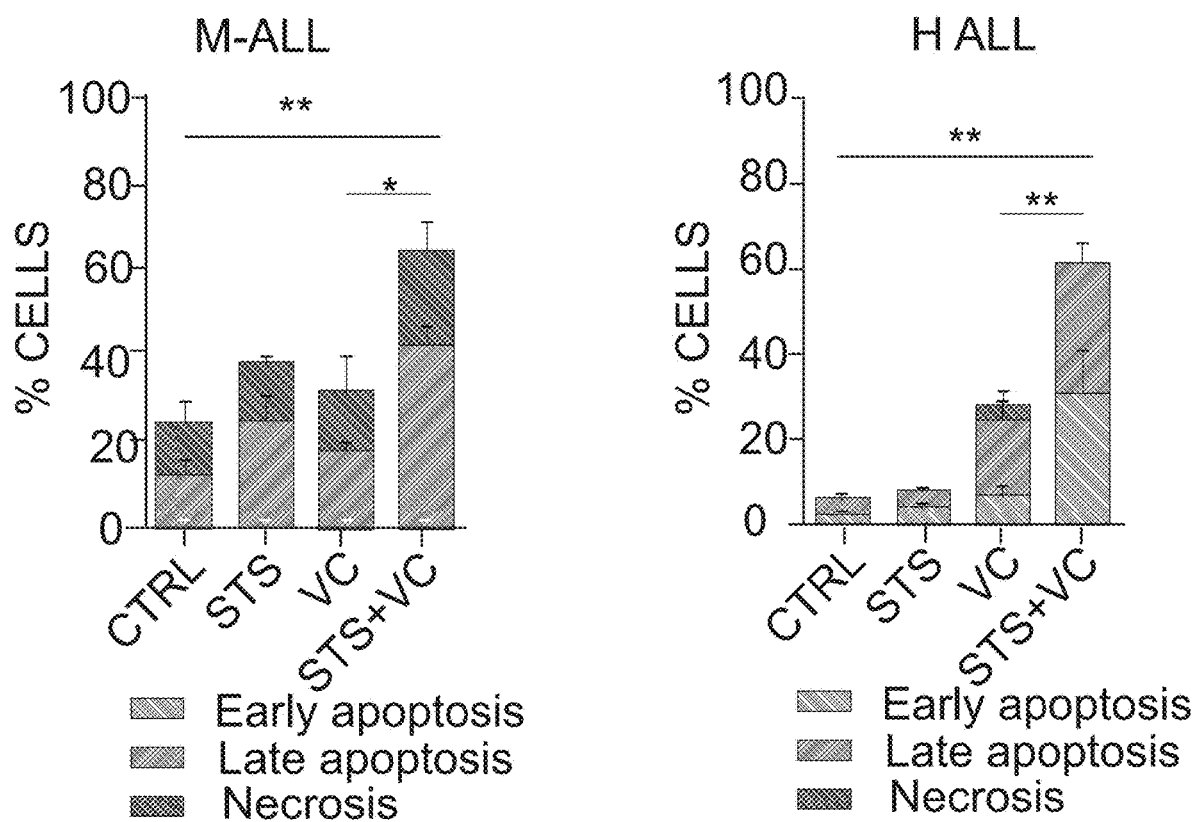
Figure 2E:
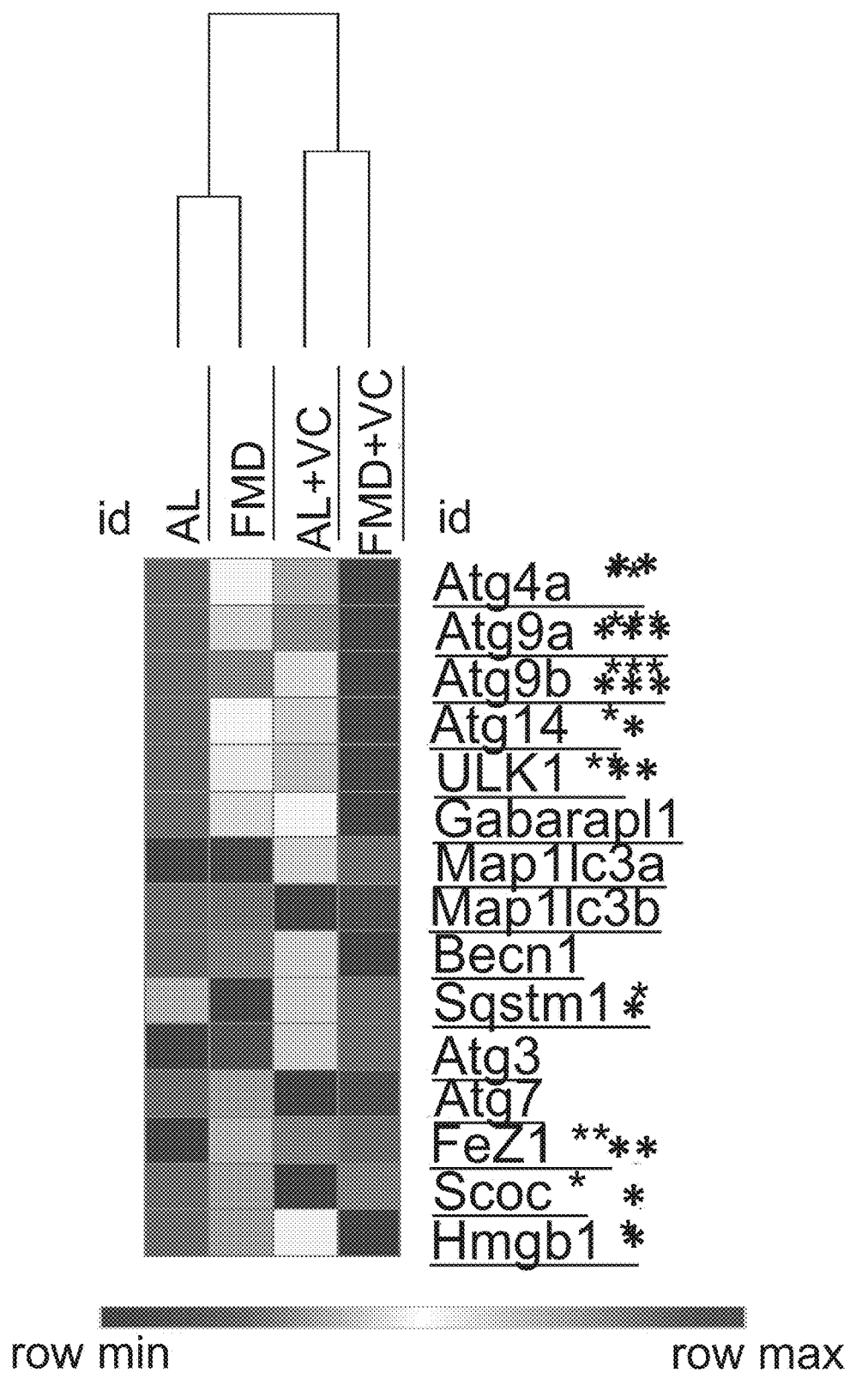
Figure 2F:
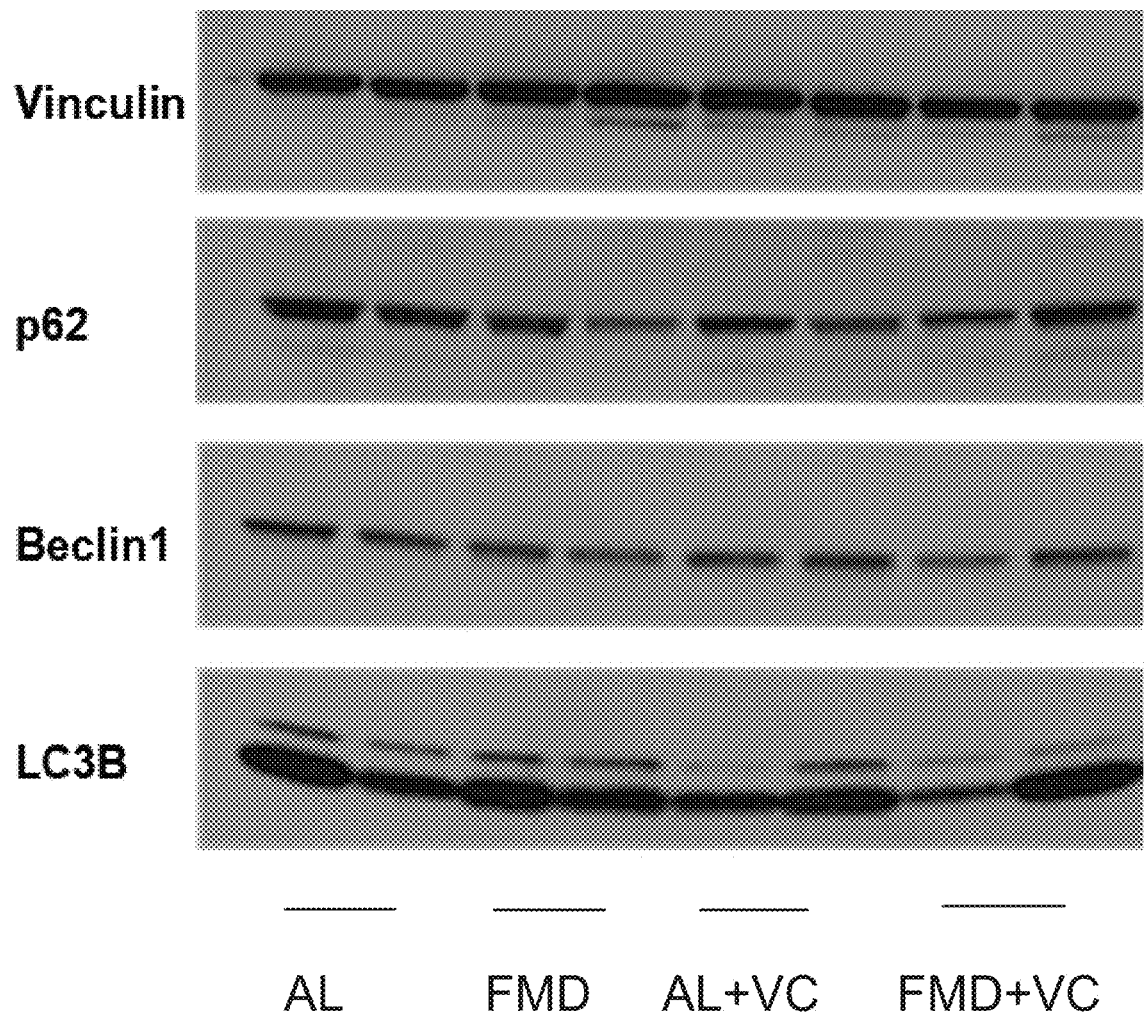
Figures 1, 2G:
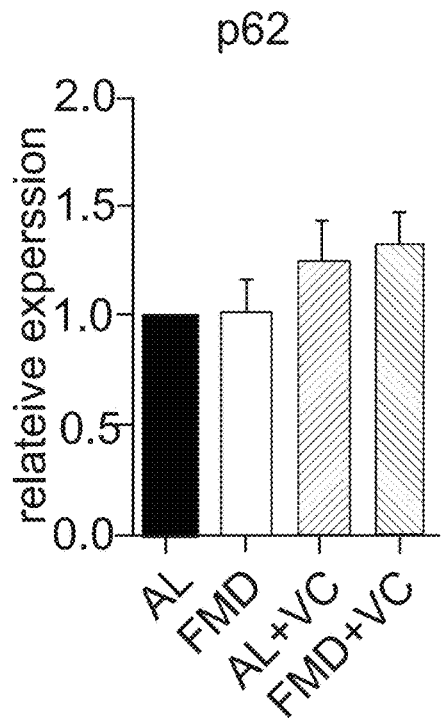
Figures 2, 2G:
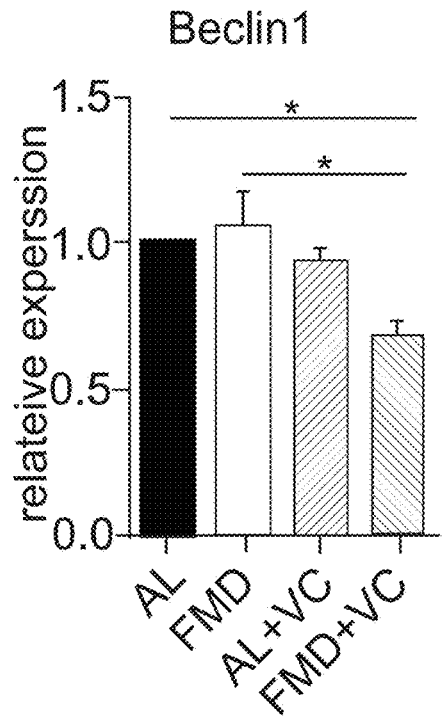

FIG. 2 shows the effects of STS in combination with vincristine in mouse and human ALL cell lines. FIGS. 2A-1 and 2A-2 provide cell count and FIGS. 2B-1 and 2B-2 show the LDH release of mouse and human ALL tumor cells were cultured in low glucose (0.5 g/l) and 2% serum (in vitro STS) or in standard glucose and 10% serum (control CTRL) medium+/−vincristine 5 nM for 48 hours. FIG. 2C provides FACS analyses of AnnexinV and eFluor780 viability dye of mouse and H-ALL tumor cell line and while FIGS. 2D-1 and 2D-2 provide percentage data quantification of cells in early, late apoptosis and necrosis. FIG. 2E provides a heatmap displaying autophagy gene expression in spleen tissue from AL, FMD, AL+VC and FMD+VC mouse (n=6/each group) *p<0.05,p<0.01, *p<0.001, one-way ANOVA. FIG. 2F provides protein analyses of LC3B, beclin1, p62, and vinculin in mouse spleen extract (n=6/group). FIGS. 2G-1, 2G-2, and 2G-3 provide relative protein quantification performed by densitometric analysis using ImageJ64 software Data are expressed as mean+/−s.e.m. *p<0.05, p<0.01, *p<0.001, one-way ANOVA. FIG. 2H provides protein analyses of LC3B, beclin1, p62 and tubulin with or without chloroquine (CQ) 100 EM in mouse and H-ALL cell lines. FIGS. 2I-1 to 2I-6 provide relative protein quantification performed by densitometric analysis using ImageJ64 software. Data are expressed as mean+/−s.e.m. *p<0.05, p<0.01, *p<0.001, one-way ANOVA.

Figures 2, 2G, 3:
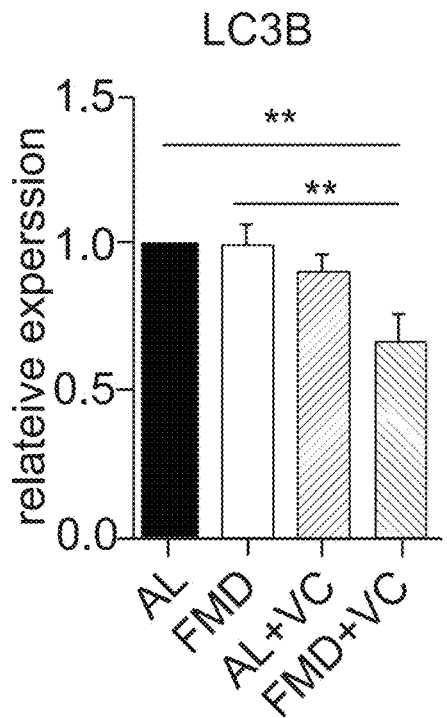
Figure 2H:
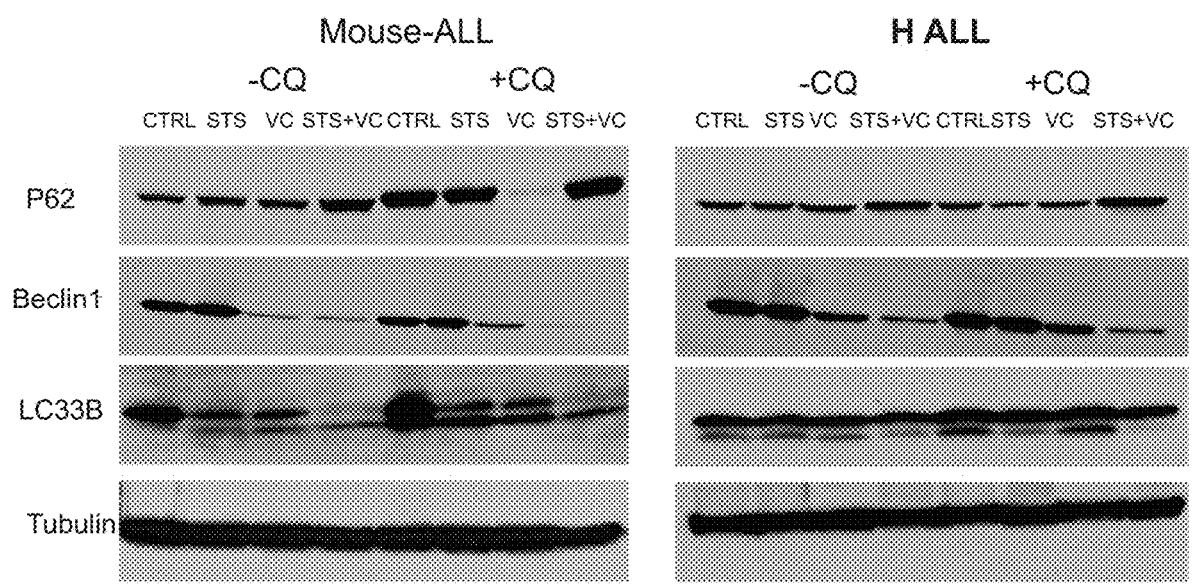
Figures 1, 2, 2I, 3:
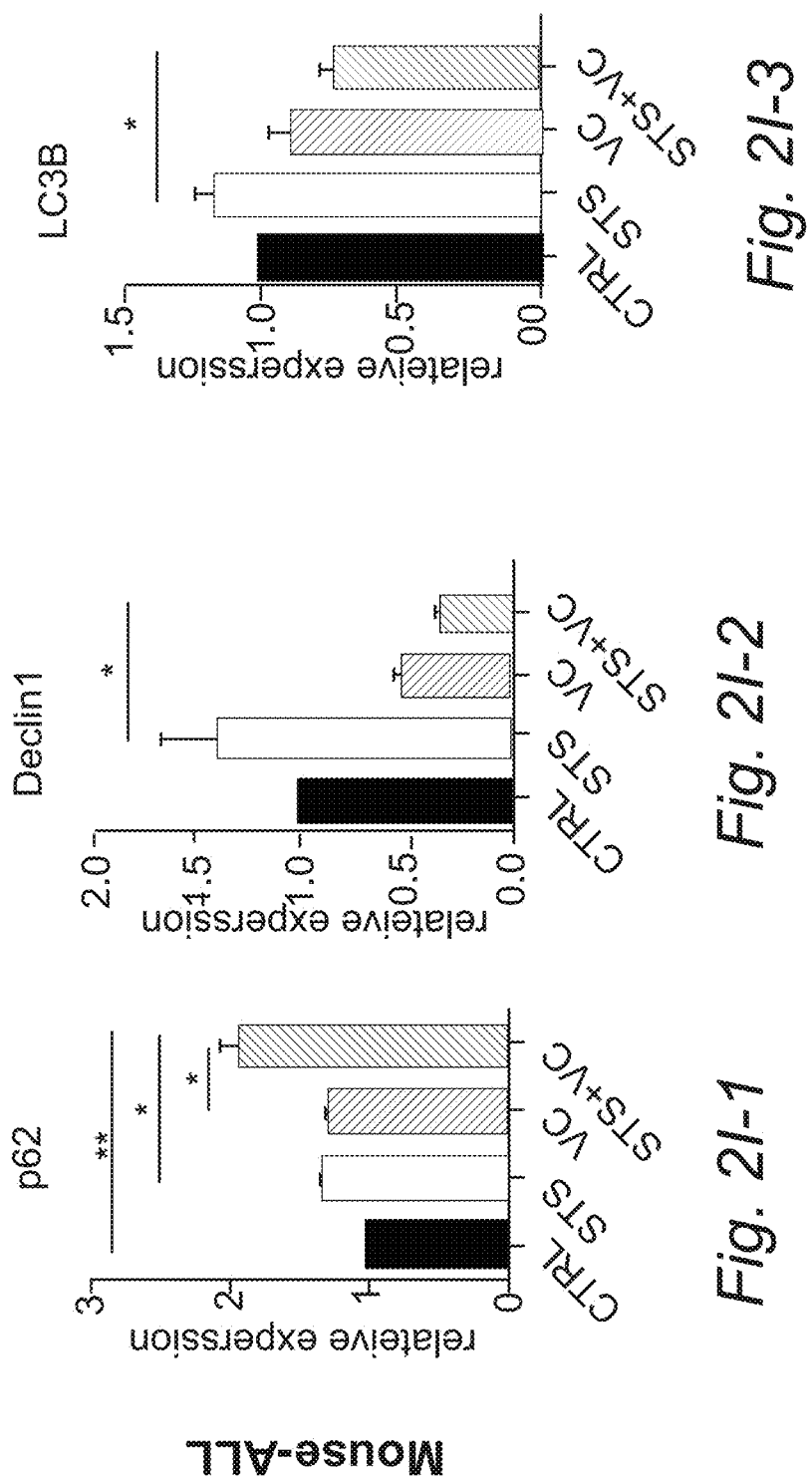
Figure 3A:
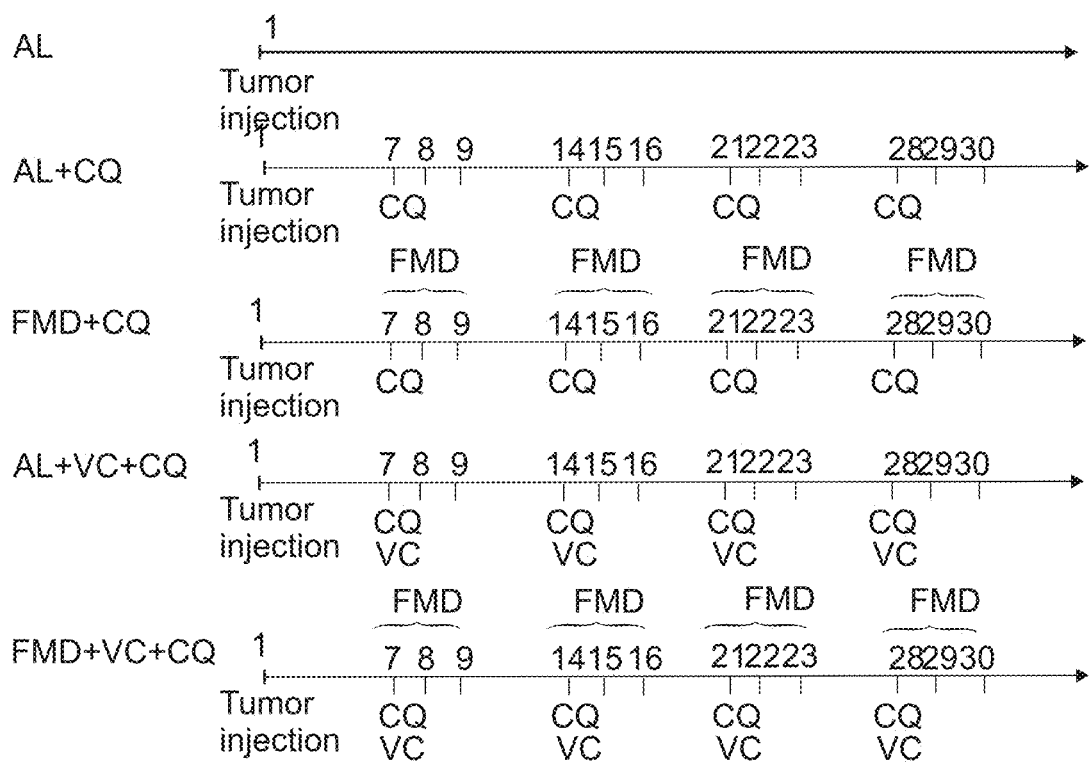
Figure 3B:
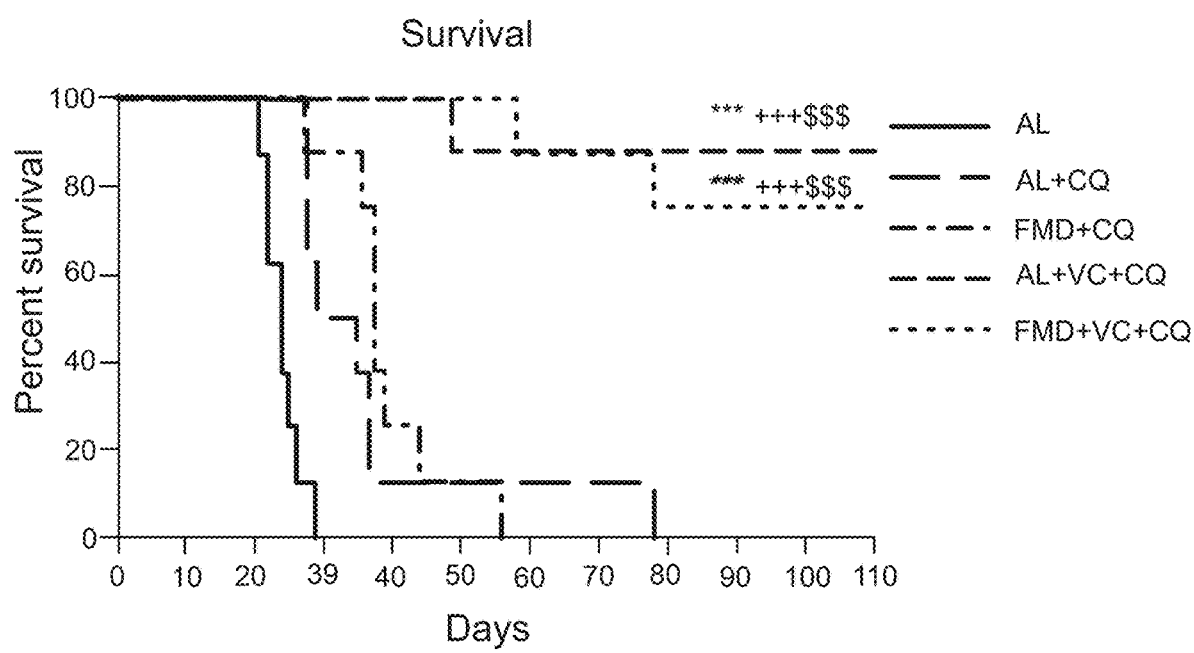
Figure 3C:
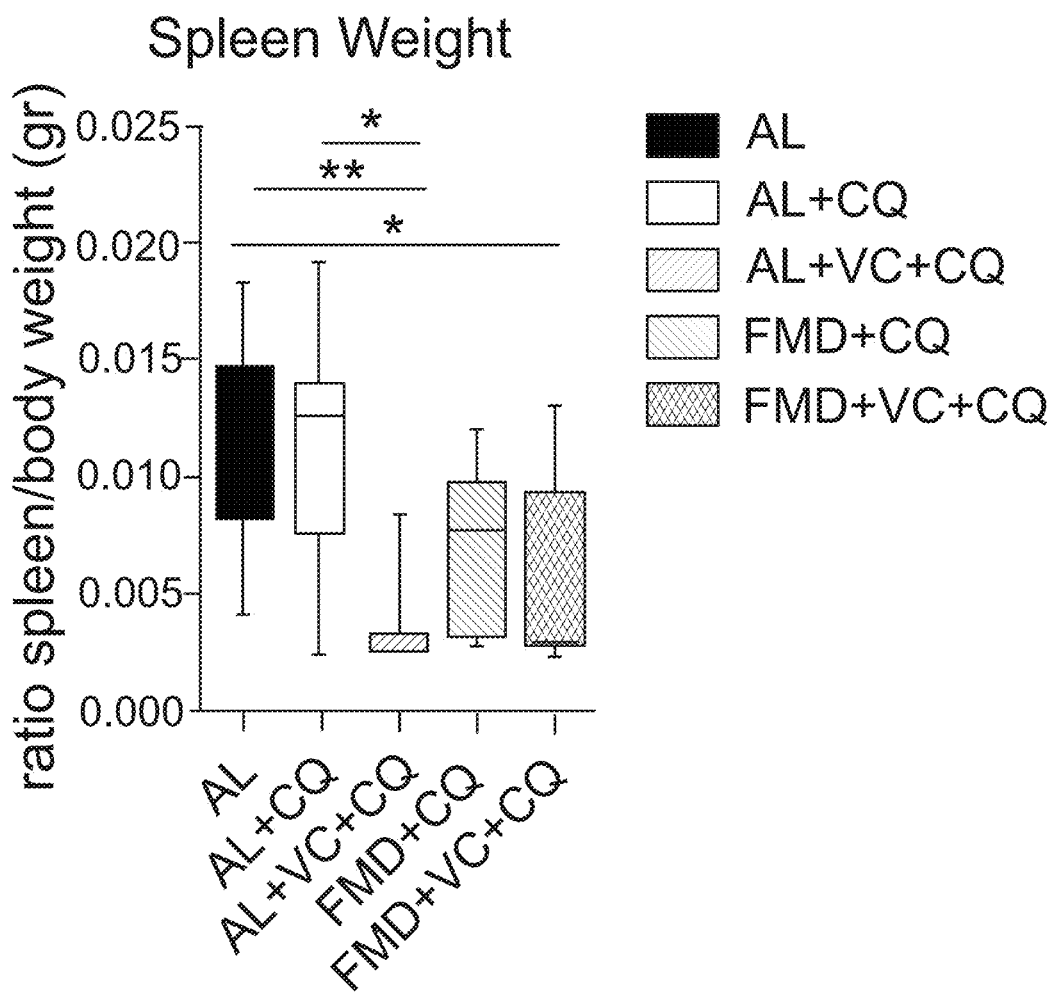
Figures 1, 2, 3D:
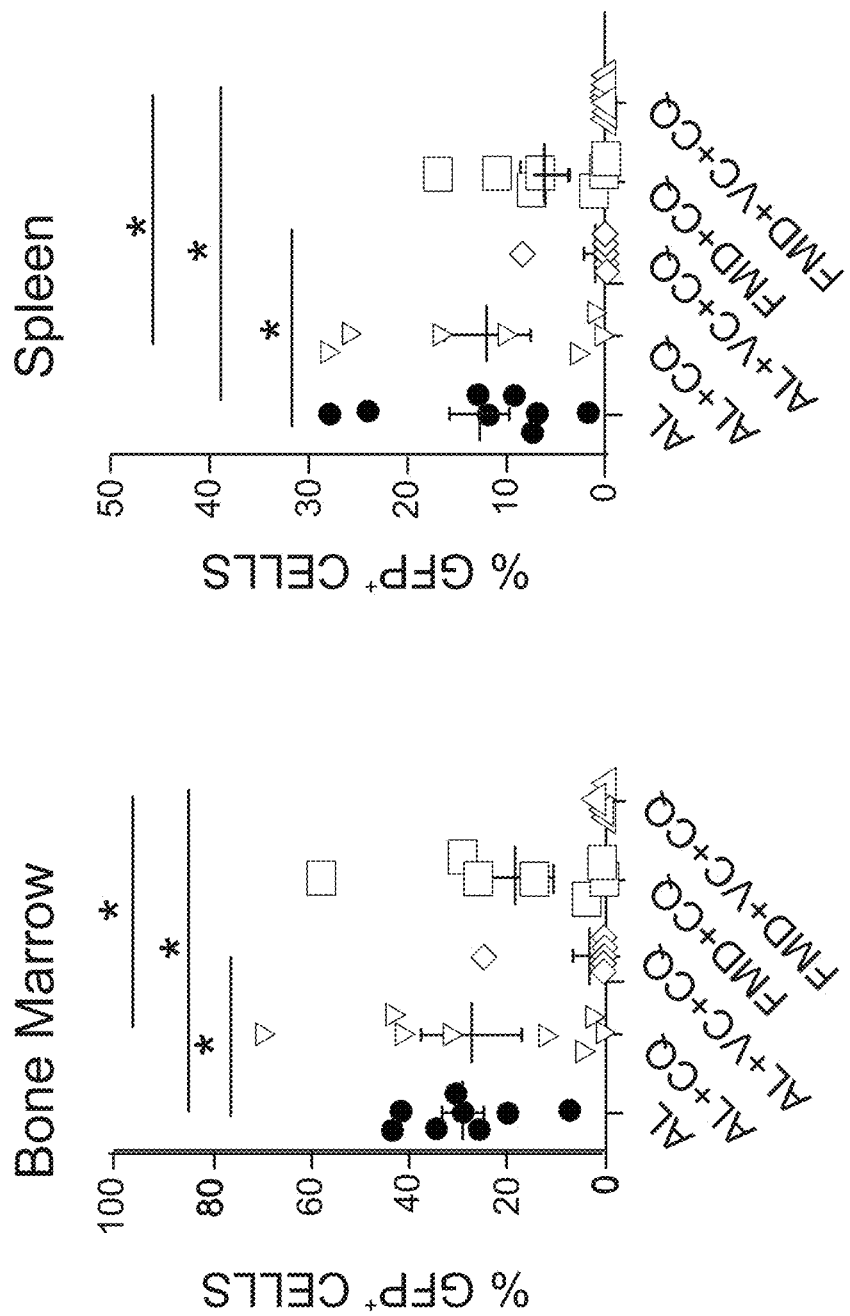
Figures 1, 3E:
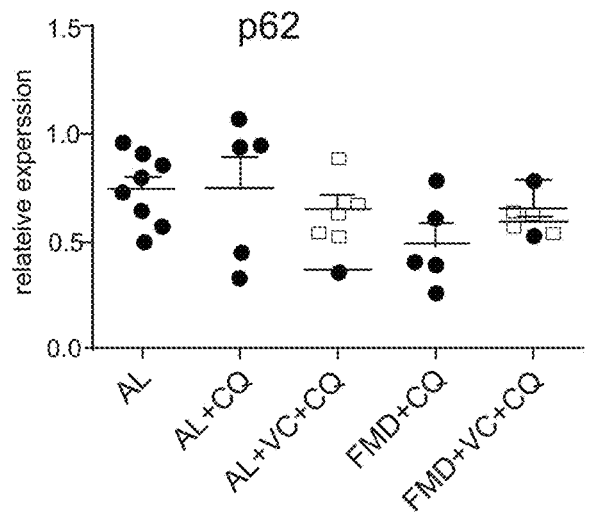
Figures 2, 3E:
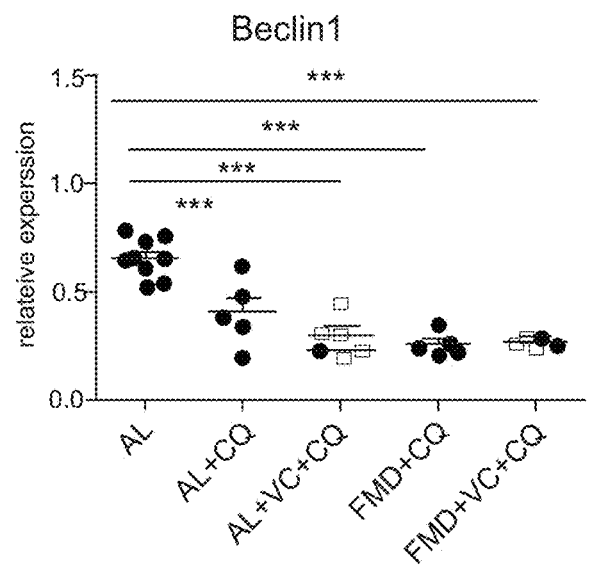
Figures 3, 3E:
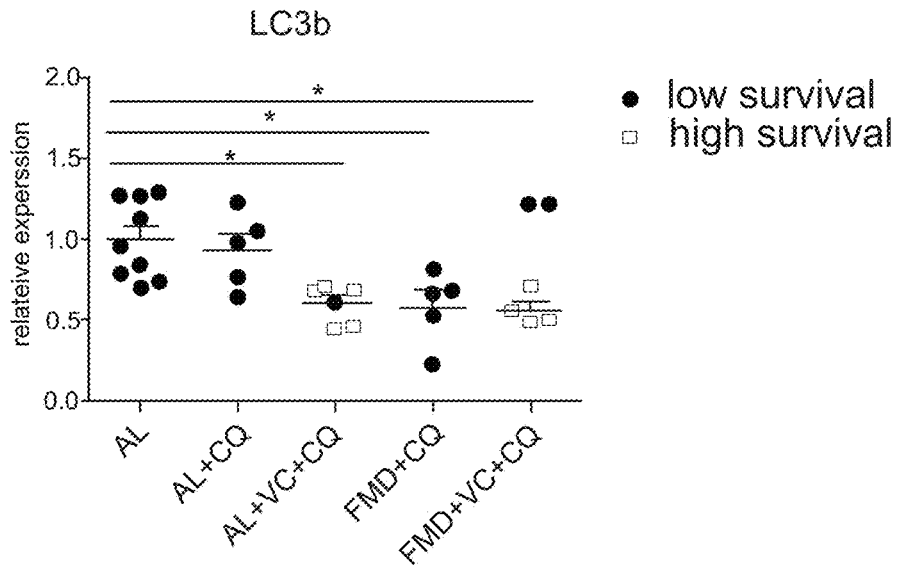

FIG. 3 shows the effect of FMD in combination with vincristine and chloroquine in in vivo model of ALL. FIG. 3A provides the experimental scheme. FIG. 3B provides a survival curve of periodical FMD and vincristine in ALL in vivo model. 40 mice C57BL/6J (20 weeks old) were injected via retro-orbital injection with $1 \times 10^4$ GFP-expressing BCR/ABL syngeneic leukemia cancer cells/mice. One week later, the mice were divided into 5 groups: Ad lib+vehicle (AL), Ad lib+chloroquine once a week IP 50 mg/kg/day (AL+CQ n=8), Fasting Mimicking Diet (FMD+CQ n=8) 4 cycles+ CQ, Ad lib+VC+CQ once a week (AL+VC+CQ n=8), and FMD+VC+CQ (n=8). (p<0.05 * vs AL, +vs AL+CQ, $ vs FMD+CQ). FIG. 3C shows the spleen weight for each of the groups in FIG. 3B. FIGS. 3D-1 and 3D-2 show quantification for GFP+ tumor cells in bone marrow and spleen by FACS analyses. FIGS. 3E-1, 3E-2, and 3E-3 show the relative quantifications of LC3B, beclin1, p62 and vinculin in mouse spleen extract performed by densitometric analysis using ImageJ64 software. Data are expressed as mean+/−s.e.m. *p<0.05, p<0.01, *p<0.001, one-way ANOVA.

Figures 2, 2I, 3, 4, 5, 6:
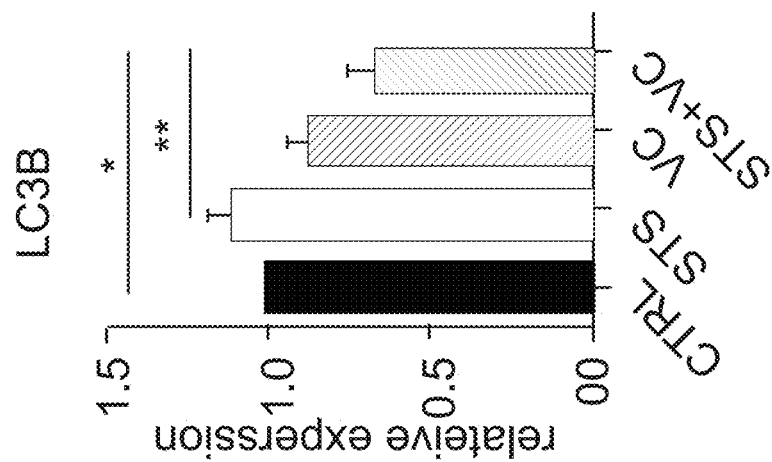
Figures 2, 2I, 3, 4, 5:
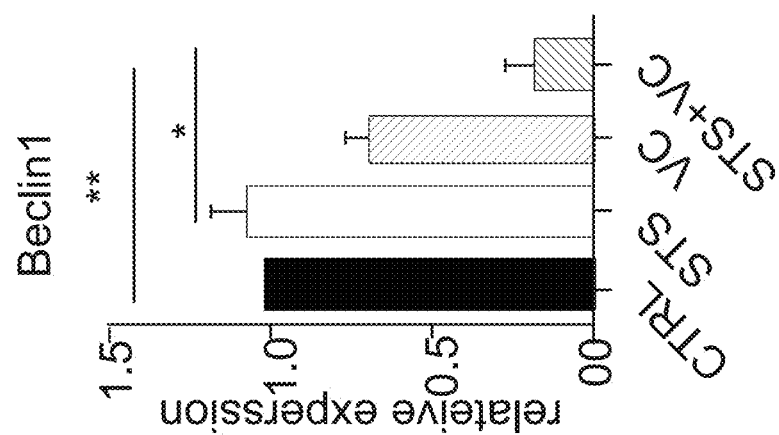
Figures 2, 2I, 3, 4:
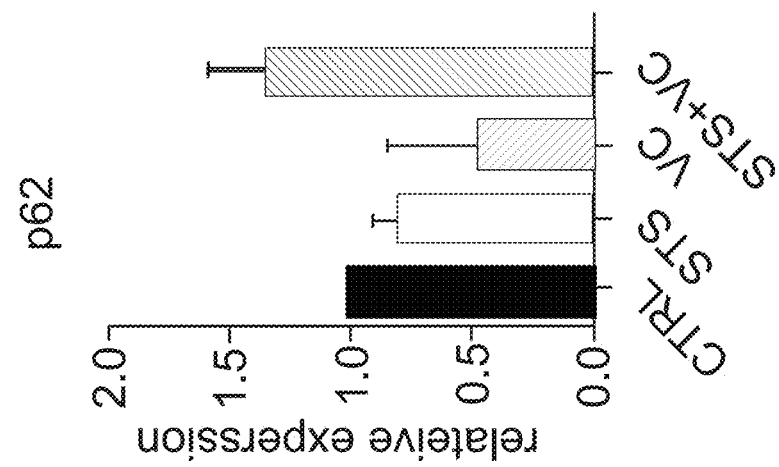
Figures 1, 4A:
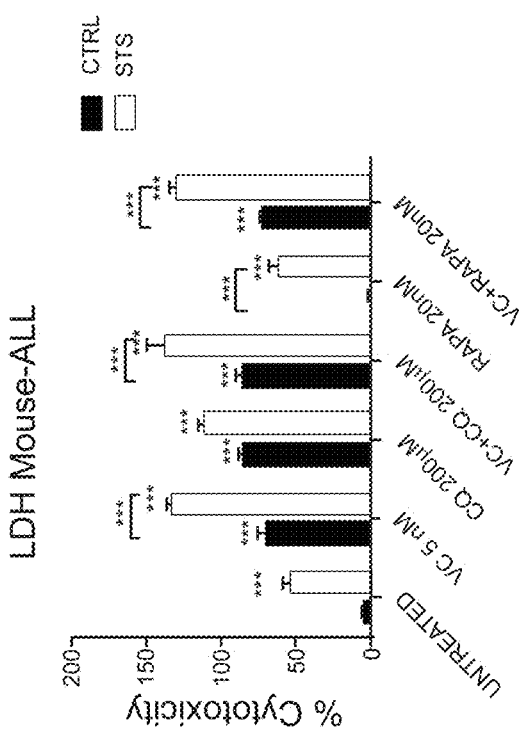
Figures 2, 4A:
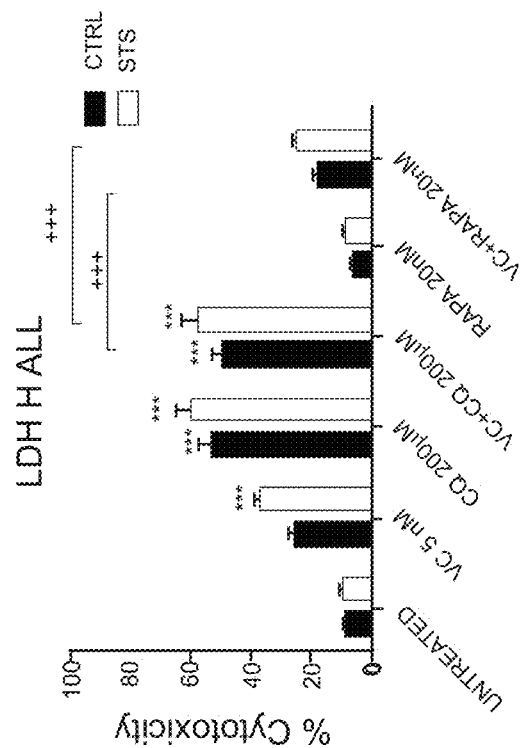
Figures 2, 4B:
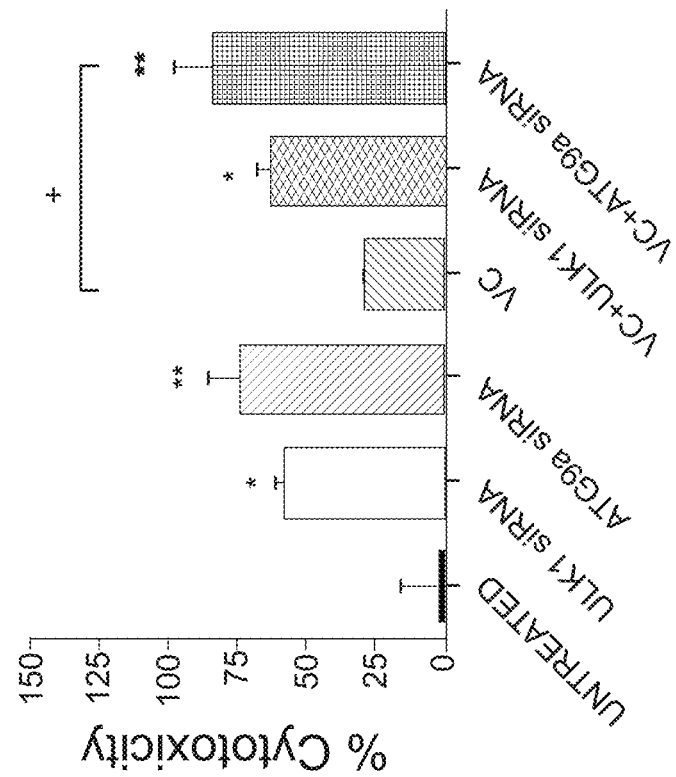
Figures 1, 4B:
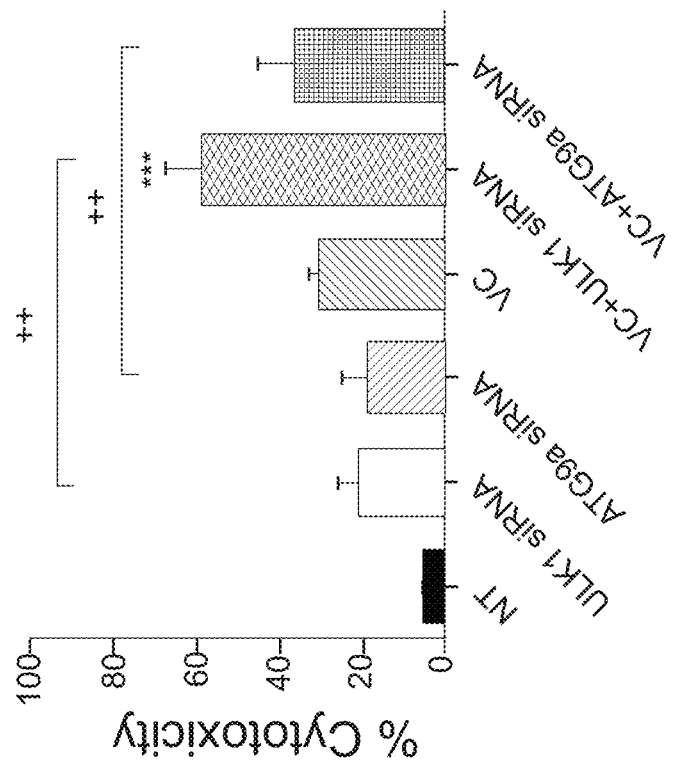
Figures 1, 4C:
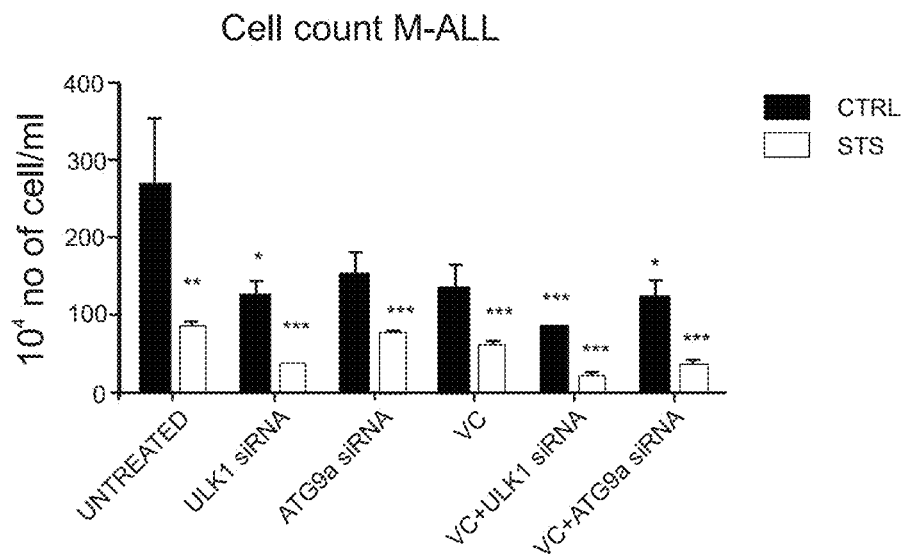
Figures 2, 4C:
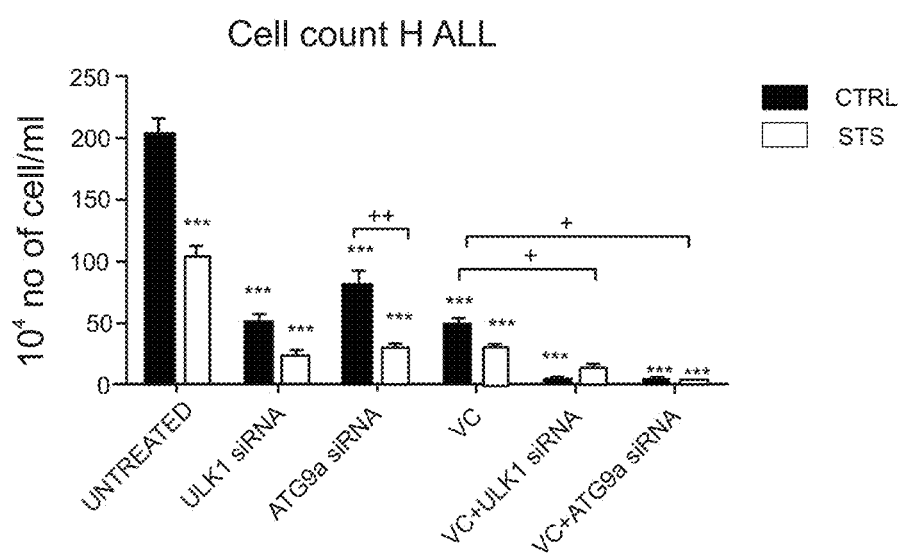
Figure 4D:
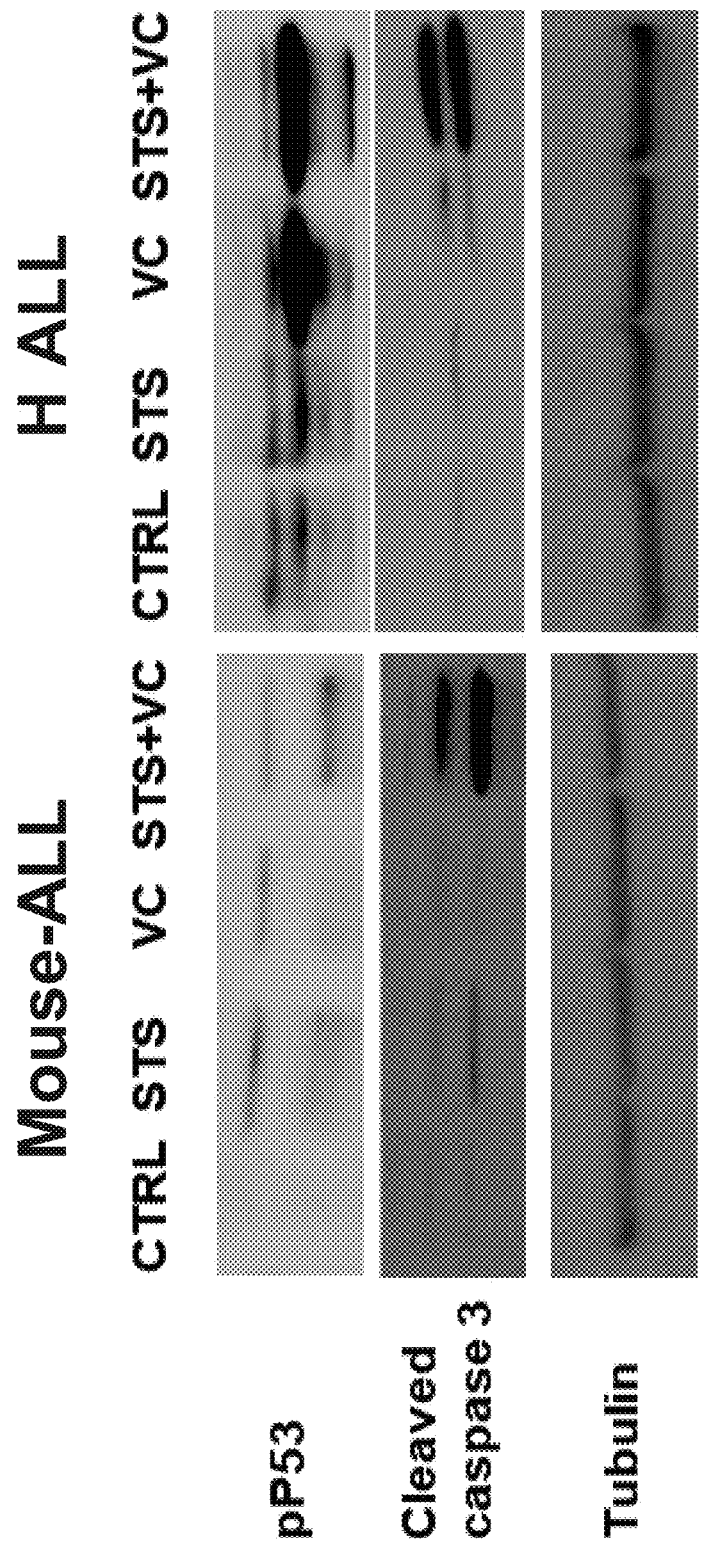
Figures 1, 4E:
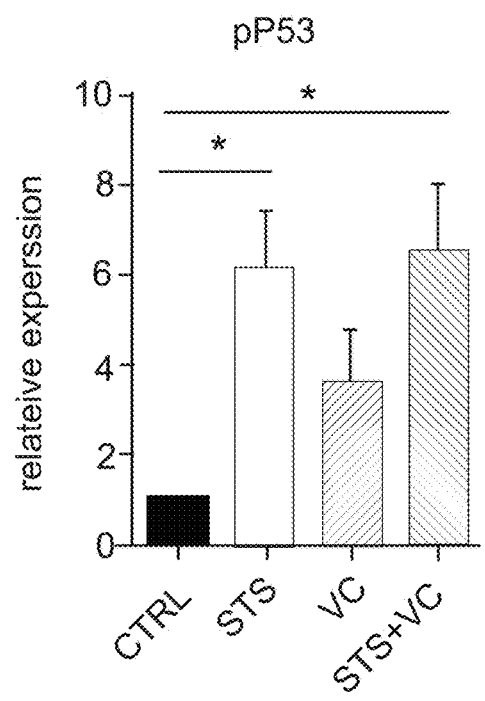
Figures 2, 4E:
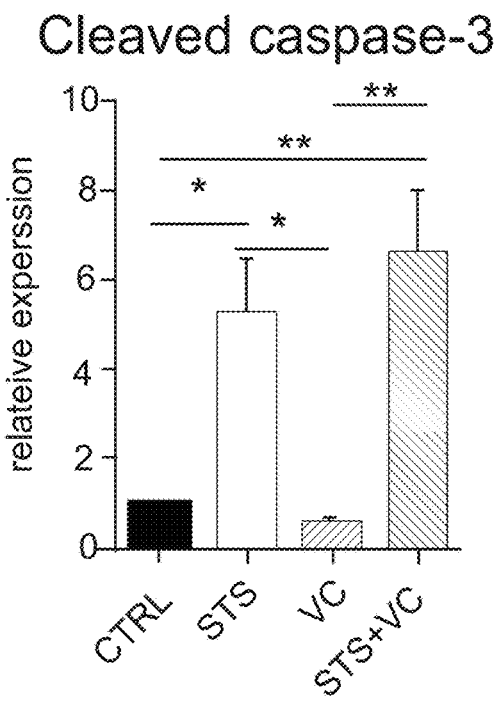
Figures 3, 4E:
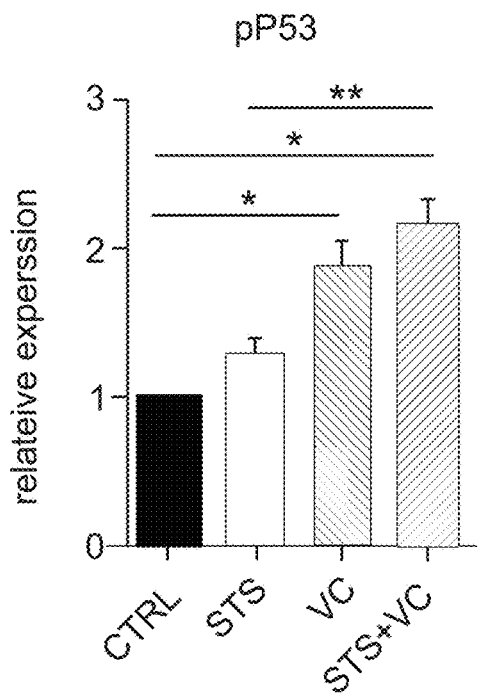
Figures 4, 4E:
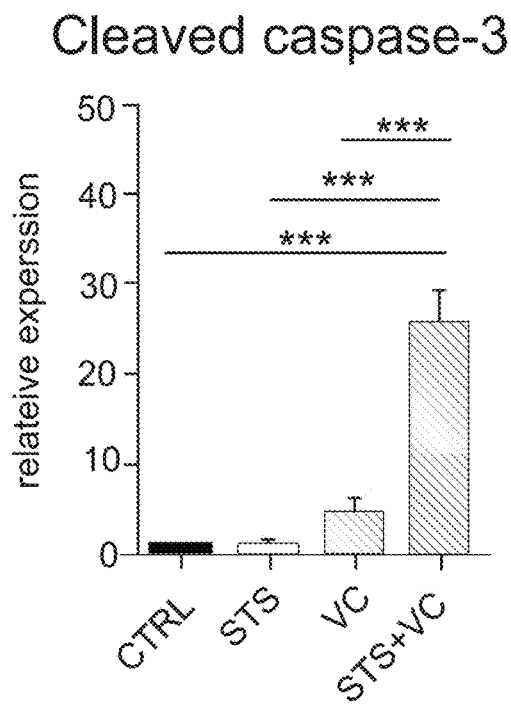

FIG. 4 provides in vitro effects of STS in combination with vincristine on autophagy and apoptosis pathway. FIGS. 4A-1 and 4A-2 provide an evaluation of LDH release to assess cell viability and cytotoxicity in mouse and human ALL cell lines. ALL tumor cells were cultured in low glucose (0.5 g/l) and 2% serum (in vitro STS) or in standard glucose and 10% serum (control CTRL) medium+/−vincristine 5 nM for 48 hours with or without chloroquine (CQ) 20004 or rapamycin (RAPA) 20 nM. FIGS. 4B-1 and 4B-2 provide an evaluation of LDH release to assess cell viability and cytotoxicity in mouse and human ALL cell lines after transfection with ULK1 siRNA (30 pM) or ATG9a (30 pM) siRNA with or without VC. FIGS. 4C-1 and 4C-2 provide cell count of H-ALL tumor cells were cultured in STS or in CTRL medium after 48 h transfection with ULK1 siRNA (30 pM) or ATG9a (30 pM) siRNA+/−VC 5 nM. FIG. 4D provides protein analyses of ULK1, ATG9a, and tubulin after 48 h of transfection with the specific siRNA (Si) in normal medium. FIGS. 4E-1 to 4E-4 provide western blot analyses and E.) relative protein quantification of phosphorylated p53, cleaved caspase 3 and tubulin in M-ALL and H-ALL cells. Data are expressed as mean+/−s.e.m. *p<0.05, p<0.01, *p<0.001, +p<0.05, ++p<0.01, +++p<0.001 one-way ANOVA.

Figure 5A:
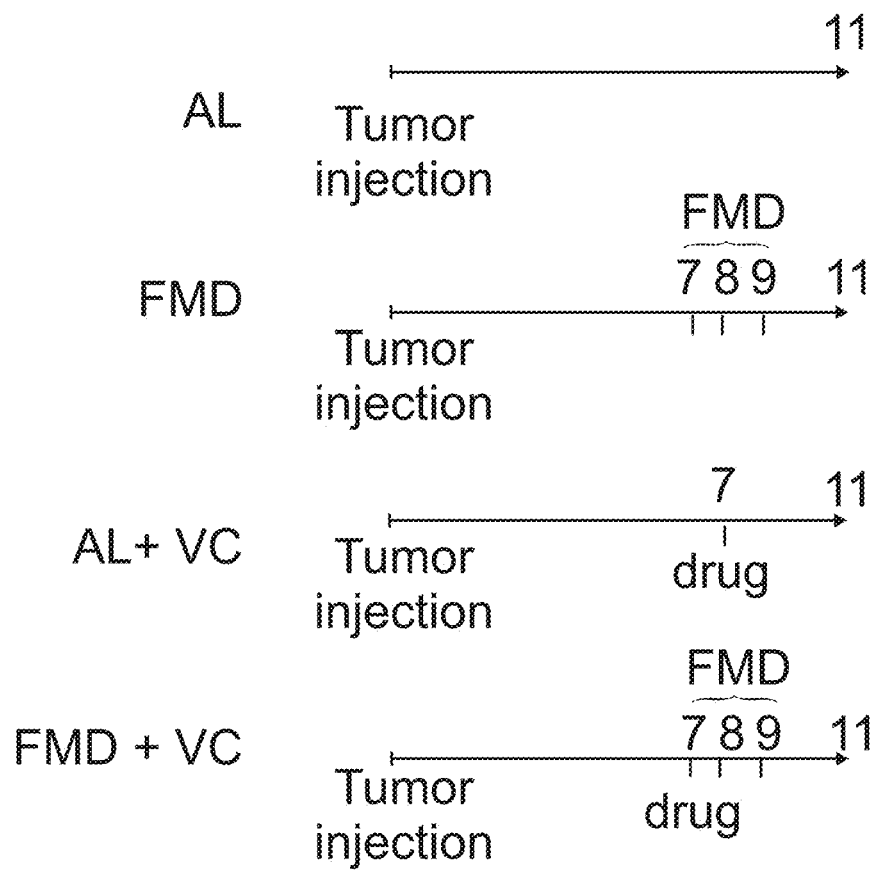
Figures 5, 5B, 6, 7, 8, 9:
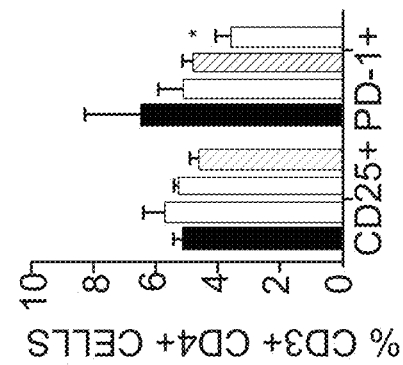
Figures 5, 5B, 6, 7, 8:
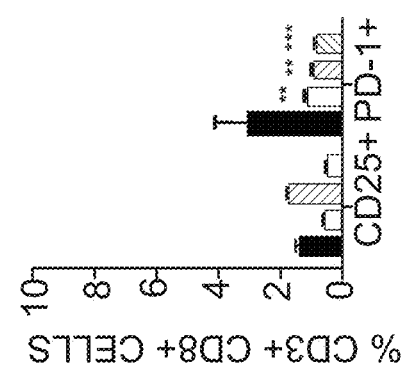
Figures 5, 5B, 6, 7:
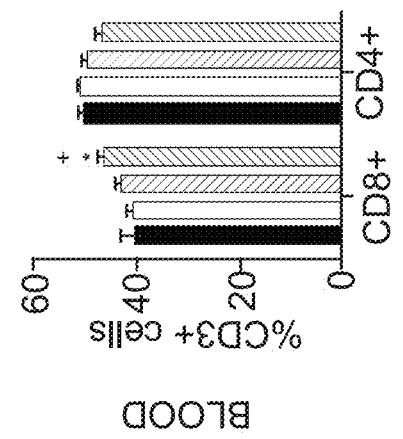
Figure 5C:
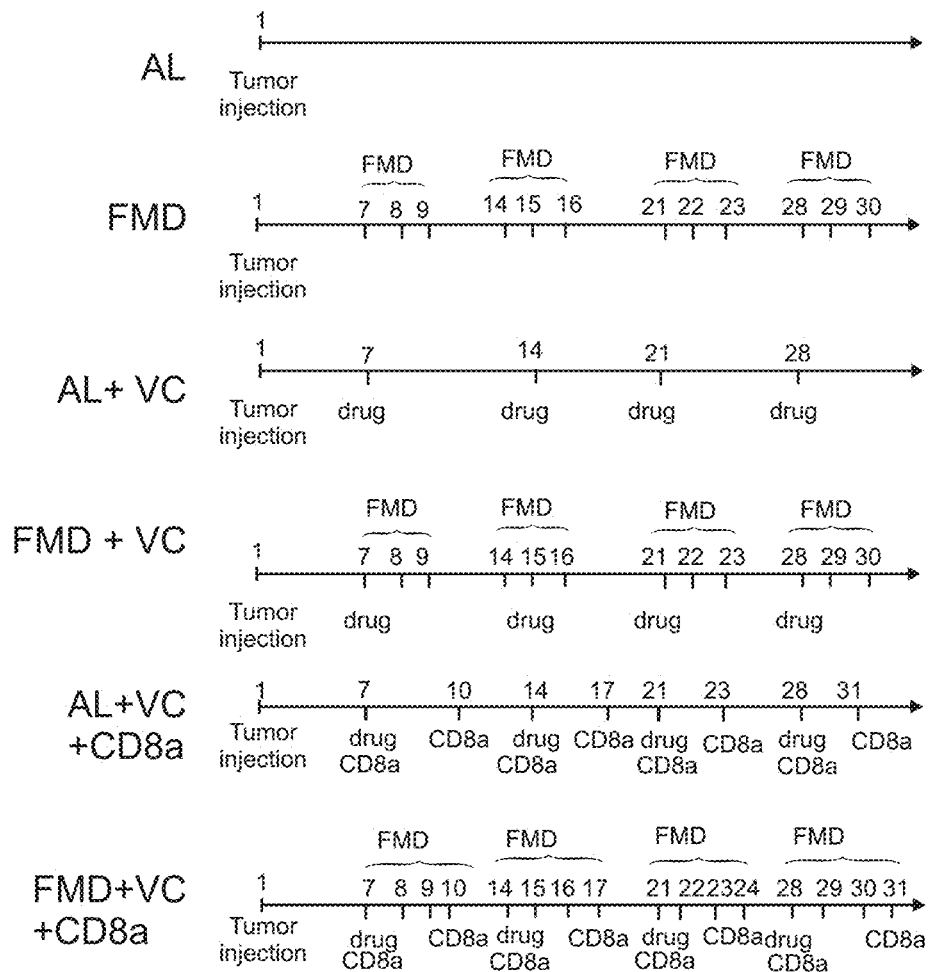
Figure 5D:
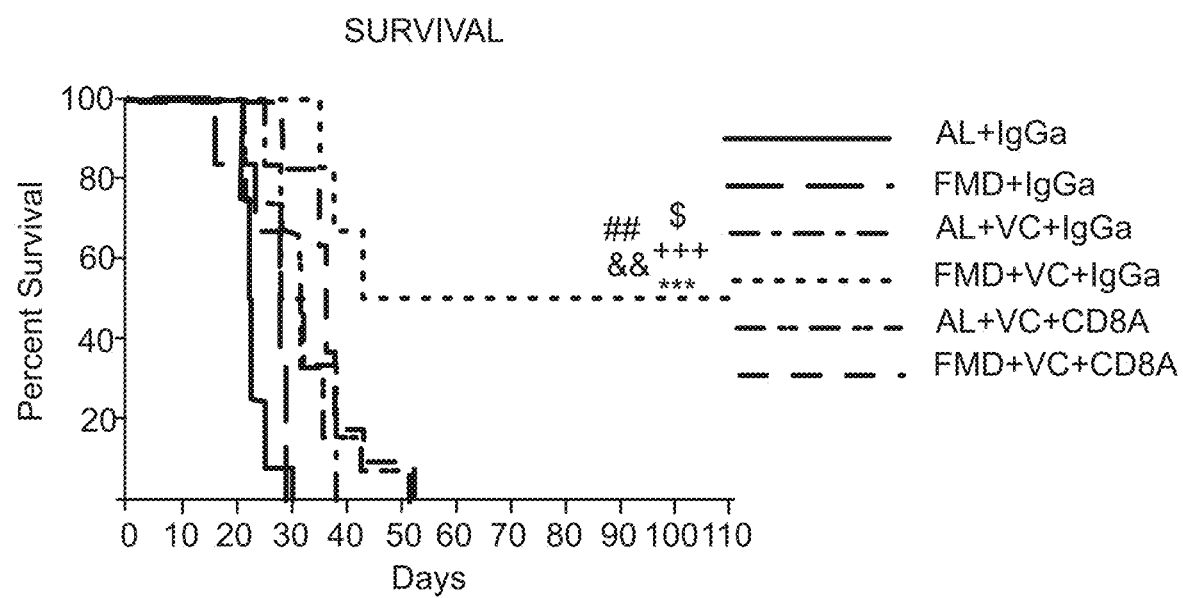
Figure 5E:
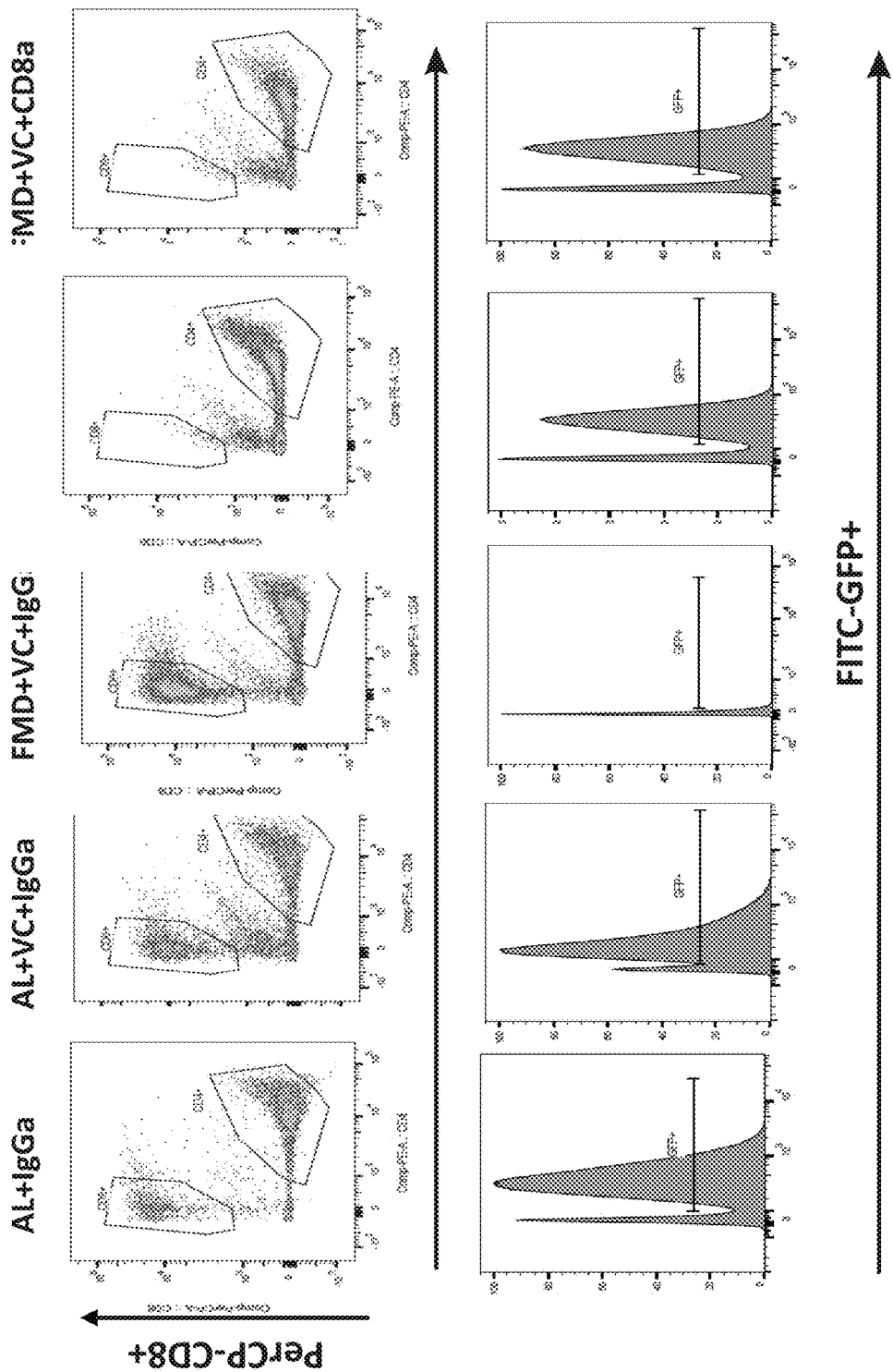

FIG. 5 shows the effects of FMD in combination with vincristine on immune response FIG. 5A shows the experimental scheme of one cycle of FMD and vincristine in ALL in vivo model (n=24) FIGS. 5B-1 to 5B-9 provide FACS analyses quantification for CD3+CD4+, CD3+CD8+, CD3+CD4+PD-1+, CD3+CD4+CD25+,CD3+CD8+PD-1+ and CD3+CD8+CD25+ in bone marrow, spleen and blood. Data are expressed as mean+/−s.e.m. *p<0.05, p<0.01, *p<0.001 vs CTRL, +p<0.05, ++p<0.01, ++p<0.001 vs FMD, $ p<0.05 vs VC one-way ANOVA. FIG. 5C provides the experimental scheme and 5D provides survival curve of periodical FMD and VC in ALL in CD8+ in vivo depletion model. 54 mice C57BL/6J (20 weeks old) were injected via retro-orbital injection with 1×10$^4$ GFP-expressing BCR-ABL syngeneic leukemia cancer cells/mice. One week later the mice were divided into 6 groups: Ad lib+IgGa (AL+IgGa n=12), Ad lib+VC once a week (AL+VC+IgGA n=6), Ad lib+VC+CD8a (AL+VC+CD8a n=12), FMD+IgGa (n=6) FMD+VC+IgGa (n=6) and FMD+VC+CD8a (n=12). (p<0.001 *** vs AL+IgGa, +++vs FMD+IgGa, $ p<0.05 vs VC+IgGa, p<0.01 ##vs VC+CD8a, && vs FMD+VC+CD8a). FIG. 5E shows representative FACS plots for CD3+ CD4+ and CD3+CD8+ and histograms for GFP+cancer cells in the bone marrow.

Figures 1, 6A:
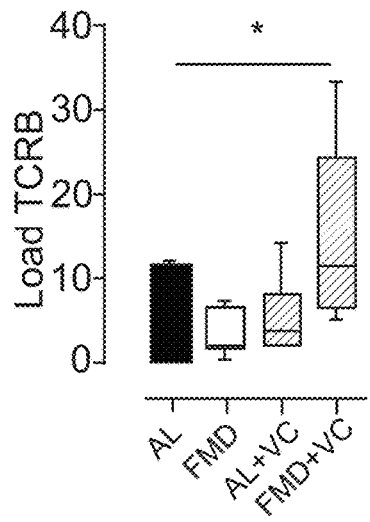
Figures 2, 6A:
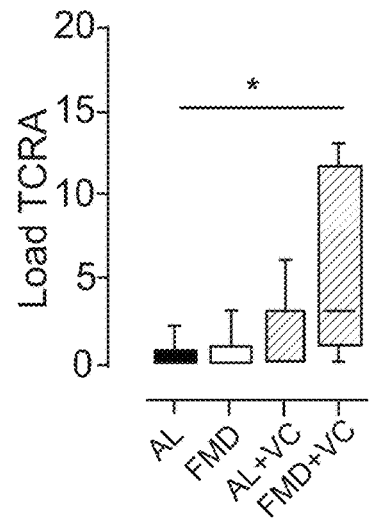
Figures 3, 6A:
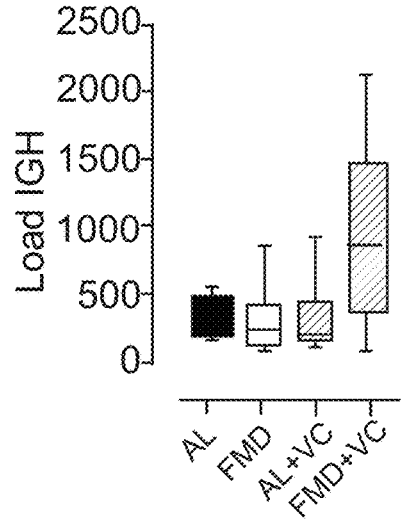
Figures 4, 6A:
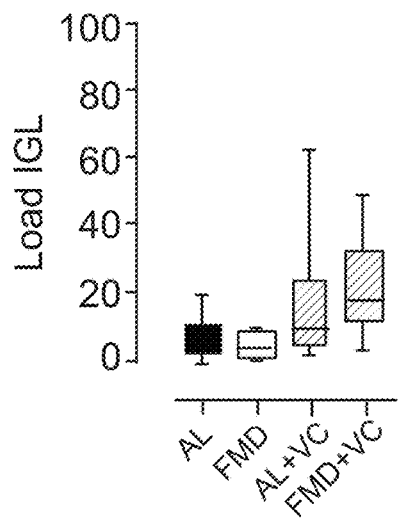
Figures 5, 6A:
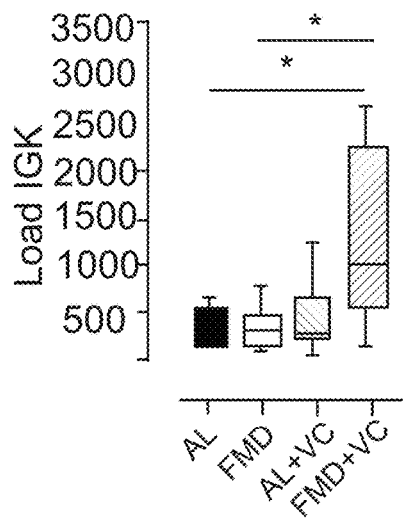
Figure 6B:
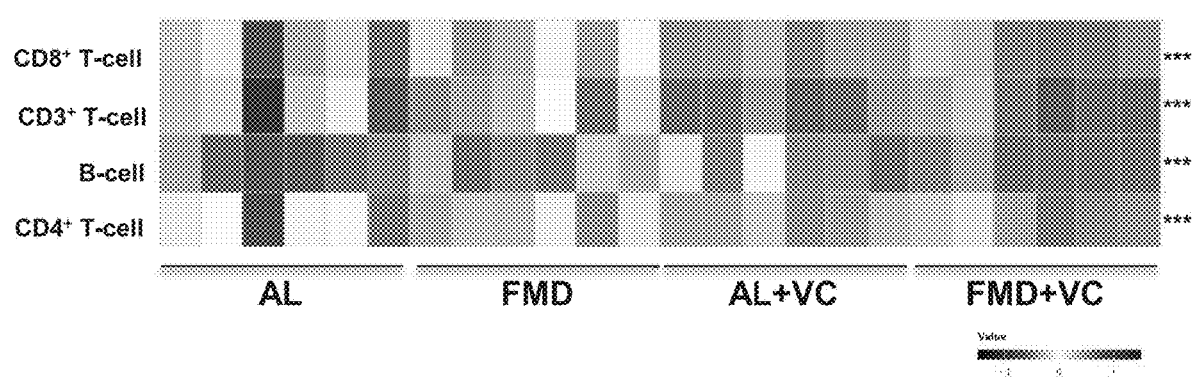
Figures 1, 6C:
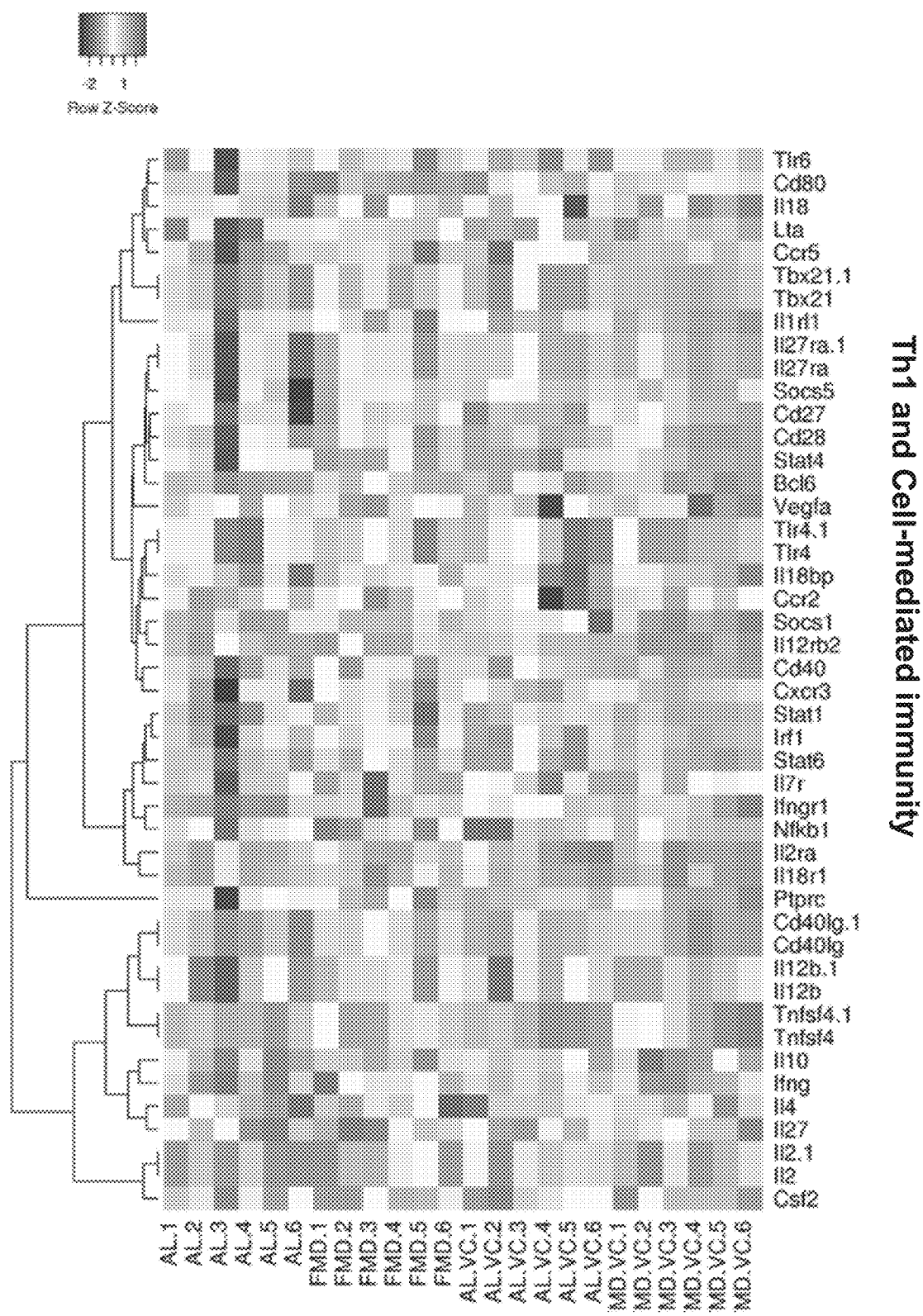
Figures 2, 6C:
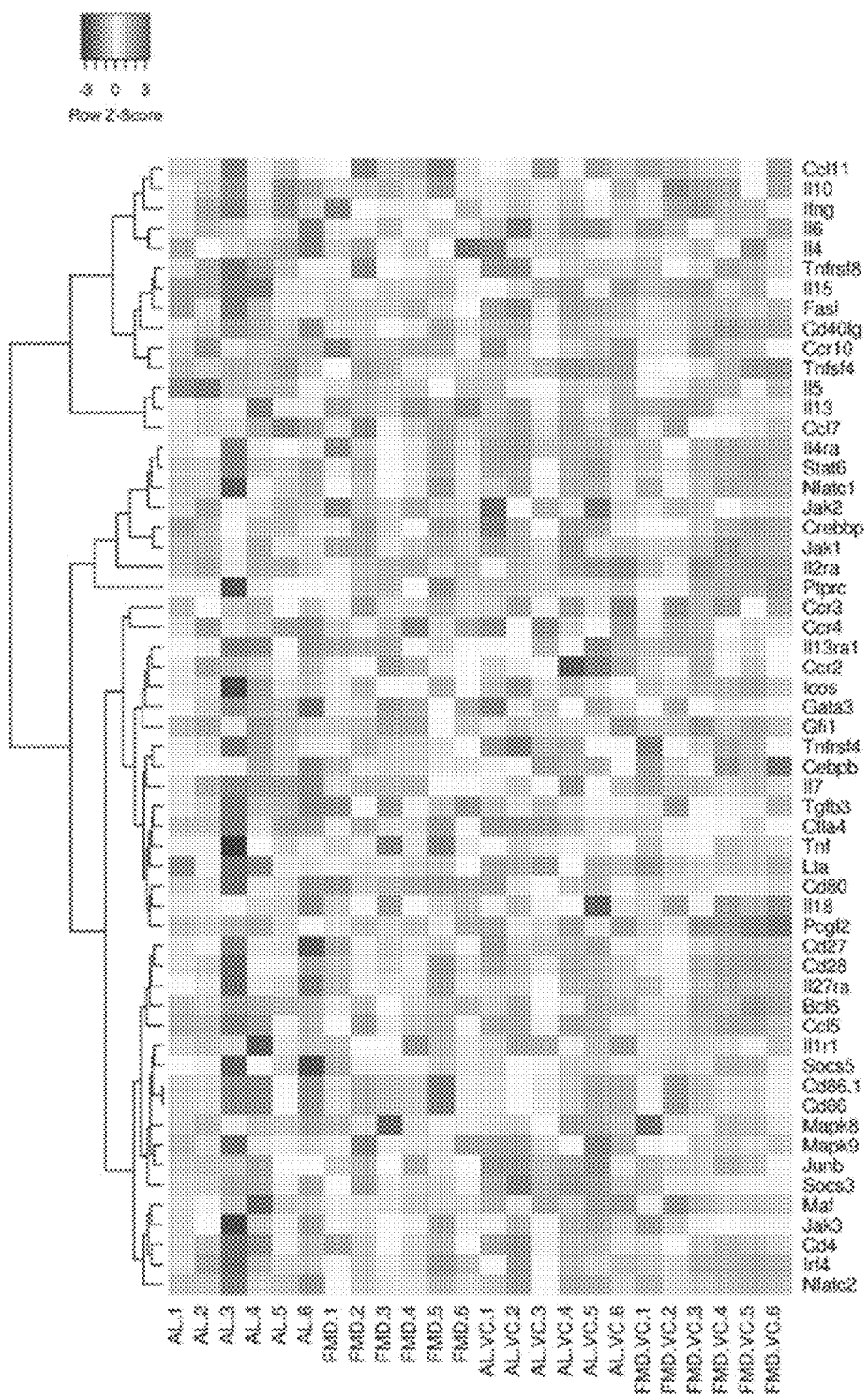
Figures 1, 6D:
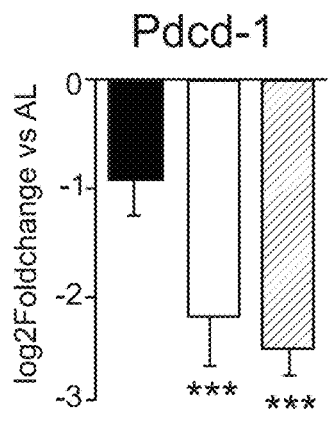
Figures 2, 6D:
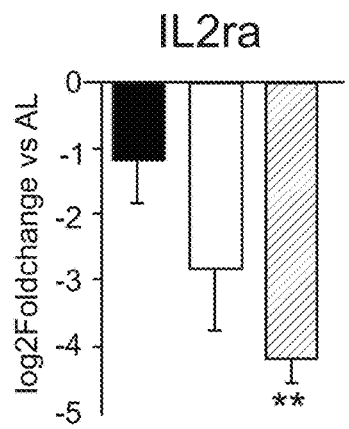
Figures 3, 6D:
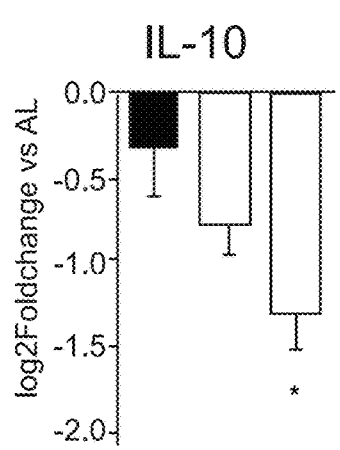
Figures 4, 6D:
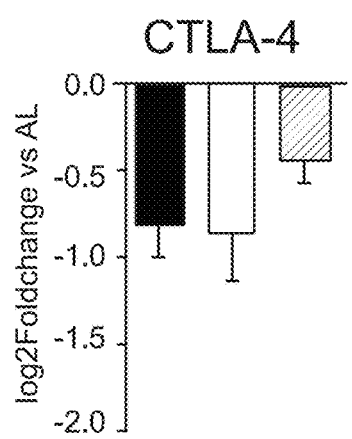
Figures 5, 6D:
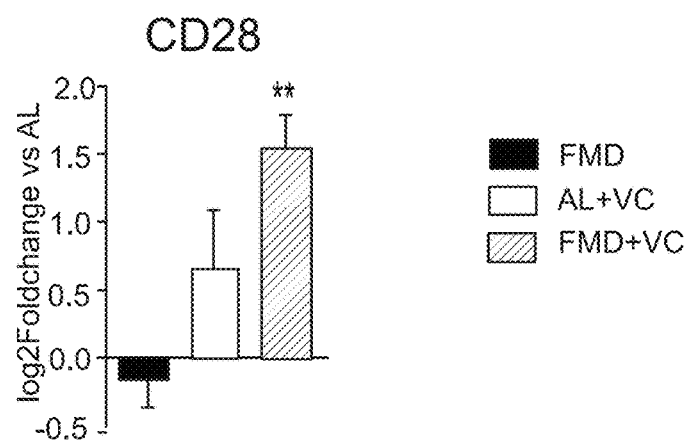

FIG. 6 shows the effects of FMD in combination with vincristine on the immune response. FIG. 6A-1 to 6A-5 provides a boxplot of T and B cell receptor repertoires in spleen tissue from AL, FMD, AL+VC and FMD+VC mouse (n=6/each group). FIG. 6B provides visualization of molecular signature from AL, FMD, AL+VC, and FMD+VC spleen (n=6/each group) using SaVanT software. Signature value refers to the average of gene expression values in a signature. Z-score (across the entire signature value matrix) is shown for the heatmap. FIGS. 6C-1 and 6C-2 provide heatmaps displaying Th1 and Th2 cells gene expression in spleen tissue from AL, FMD, AL+VC, and FMD+VC mouse (n=6/each group). Red indicates the upregulation of gene expression and blue downregulation of gene expression. The differentially expressed genes are shown on the right side of the image. FIGS. 6D-1 to 6D-5 show the Log 2 Fold Change of Pdcd-1, IL2ra, IL-10, CTLA-4, CD28 versus AL mice. Data are expressed as mean+/−s.e.m. *p<0.05, p<0.01, *p<0.001, one-way ANOVA.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES

1. Paul, S., Kantarjian, H. & Jabbour, E. J. Adult Acute Lymphoblastic Leukemia. *Mayo Clin Proc* 91, 1645-1666 (2016).
2. Friend, B. D. & Schiller, G. J. Closing the gap: Novel therapies in treating acute lymphoblastic leukemia in adolescents and young adults. Blood Rev 32, 122-129 (2018).
3. Gökbuget, N. Treatment of Older Patients with Acute Lymphoblastic Leukaemia. *Drugs Aging* (2017).
4. Raffaghello, L., et al. Starvation-dependent differential stress resistance protects normal but not cancer cells against high-dose chemotherapy. *Proc Natl Acad Sci USA* 105, 8215-8220 (2008).
5. Di Biase, S. & Longo, V. D. Fasting-induced differential stress sensitization in cancer treatment. *Mol Cell* Oncol 3, e1117701 (2016).
6. Longo, V. D. & Fontana, L. Calorie restriction and cancer prevention: metabolic and molecular mechanisms. *Trends Pharmacol Sci* 31, 89-98 (2010).
7. Safdie, F., et al. Fasting enhances the response of glioma to chemo- and radiotherapy. *PLoS One* 7, e44603 (2012).
8. Longo, V. D. & Mattson, M. P. Fasting: molecular mechanisms and clinical applications. *Cell Metab* 19, 181-192 (2014).
9. Brandhorst, S., Wei, M., Hwang, S., Morgan, T. E. & Longo, V. D. Short-term calorie and protein restriction provide partial protection from chemotoxicity but do not delay glioma progression. *Exp Gerontol* 48, 1120-1128 (2013).
10. Di Biase, S., et al. Fasting-Mimicking Diet Reduces HO-1 to Promote T Cell-Mediated Tumor Cytotoxicity. *Cancer Cell* 30, 136-146 (2016).
11. Lee, C., et al. Fasting cycles retard growth of tumors and sensitize a range of cancer cell types to chemotherapy. *Sci Transl Med* 4, 124ra127 (2012).
12. Brandhorst, S., et al. A Periodic Diet that Mimics Fasting Promotes Multi-System Regeneration, Enhanced Cognitive Performance, and Healthspan. *Cell Metab* 22, 86-99 (2015).
13. Cheng, C. W., et al. Fasting-Mimicking Diet Promotes Ngn3-Driven beta-Cell Regeneration to Reverse Diabetes. *Cell* 168, 775-788.e712 (2017).

What is claimed is:

1. A method comprising:
   administering a fasting-mimicking diet to a subject having leukemia, wherein the fasting-mimicking diet is formulated to provide 800 to 1250 kcal on day 1 and 500 to 950 kcal on days 2, 3, 4, 5, and any additional days and to provide, less than 30 g of sugar for each day of the fasting-mimicking diet, less than 30 g of proteins for each day of the fasting-mimicking diet, 15-30 grams of monounsaturated fats for each day of the fasting-mimicking diet, 2-10 g of polyunsaturated fats for each day of the fasting-mimicking diet, and less than 12 g of saturated fats for each day of the fasting-mimicking diet and wherein the amount of carbohydrates on day 1 is greater than the amounts provided for days 2, 3, 4, 5, and any additional days, wherein the fasting-mimicking diet is formulated to provide at least 60% calories from fatty acids and wherein at least 50% of the calories from fatty acids are from coconut oil and tree nuts.

2. The method of claim 1, wherein the subject has lymphoblastic leukemia.

3. The method of claim 1 wherein the fasting-mimicking diet is administered in combination with a chemotherapeutic agent and/or an autophagy inhibitor, the chemotherapeutic agent and/or the autophagy inhibitor being administered during administration of the fasting-mimicking diet.

4. The method of claim 3 wherein the chemotherapeutic agent includes a component selected from the group consisting of vincristine, cyclophosphamide, anthracycline, corticosteroids, L-asparaginase, and combination thereof.

5. The method of claim 4, wherein the anthracycline is daunorubicin or doxorubicin.

6. The method of claim 4, wherein the corticosteroids is selected from the group consisting of prednisone, dexamethasone, and combinations thereof.

7. The method of claim 4, wherein the autophagy inhibitor is chloroquine or hydroxychloroquine.

8. The method of claim 1, wherein the fasting-mimicking diet includes lyophilized vegetable soups, bars, olives, crackers, herbal teas, supplements of vitamins and minerals.

9. The method of claim 1, wherein the fasting-mimicking diet is administered for 6, 7, 8, 9, or 10 days.

10. The method of claim 1, wherein for day 1, the fasting-mimicking diet is formulated to provide 3.5 to 5 kcal per pound of the subject.

11. The method of claim 10, wherein for day 1, the fasting-mimicking diet is formulated to provide less than 25 g of sugar, less than 23 g of proteins, 16-25 grams of monounsaturated fats, 4.8 to 8 g of polyunsaturated fats, and 1 to 10g of saturated fats.

12. The method of claim 11 wherein for days 2, 3, 4, 5, or any additional days, the fasting-mimicking diet is formulated to provide 2.4 to 4 kcal per pound of the subject.

13. The method of claim 12 wherein for days 2, 3, 4, 5, or any additional days, the fasting-mimicking diet includes less than 16 g of sugars, less than 15 g of protein, 8 to 12 g of monounsaturated fats, 2 to 4 g of polyunsaturated fats and 1 to 6 grams of saturated fats.

14. The method of claim 1, wherein the fasting-mimicking diet includes soups, nutrition bars, crackers, an optional drink with a glucose substitute, olives, vitamin and mineral supplements, algal oil, and optional teas.

15. The method of claim 14, wherein the fasting-mimicking diet includes nutrition bars and soups to be consumed for breakfast, lunch, and dinner.

16. The method of claim 15 wherein the fasting-mimicking diet includes an FMD soup formulated to provide less than about 1 gram of saturated fat per serving, less than about 5 grams of trans fat per serving, less than about 10 grams of protein per serving, less than about 40 grams of carbohydrates per serving.

17. The method of claim 16 wherein the FMD soup is formulated from any combination of components selected from the group consisting of black beans, butternut squash, *quinoa*, tomatoes, mushrooms, white beans, brown beans, spinach, green tea extract, rice flour, onions, brown rice powder, carrots, inulin, leeks, olive oil, cabbage, potatoes, olives, peas, pumpkin, maltodextrin, and celery, chicory root fiber, sea salt, yeast, basil, parsley, garlic, rosemary extract, coriander, oregano, potato starch, potato flakes, zucchini squash, turmeric.

18. The method of claim 16 wherein the FMD soup is formulated from a first component selected from the group consisting of black beans, butternut squash, *quinoa*, tomatoes, mushrooms, white beans, brown beans, spinach, and combinations thereof and a second component selected from the group consisting of green tea extract, rice flour, onions, brown rice powder, carrots, inulin, leeks, olive oil, cabbage, potatoes, olives, peas, pumpkin, maltodextrin, and celery, chicory root fiber, sea salt, yeast, basil, parsley, garlic, rosemary extract, coriander, oregano, potato starch, potato flakes, zucchini squash, turmeric, and combinations thereof.

19. The method of claim 15 wherein the fasting-mimicking diet includes a first FMD nutrition bar formulated to provide about bout 150 kcal to 350 kcal per serving, 10 to 35 grams of total fat per serving, less than about 8 grams of saturated fat per serving, less than about 5 grams of trans fat per serving, less than about 10 grams of protein per serving, and less than about 30 grams of carbohydrates per serving.

20. The method of claim 19 wherein the first FMD nutrition bar is formulated from a combination of macadamia nuts, honey, pecans, almonds, almond butter, coconut flour, sea salt, mixed tocopherols (vitamin E), citric acid, and/or ascorbic acid.

21. The method of claim 15 wherein the fasting-mimicking diet includes a second FMD nutrition bar formulated to provide about 70 kcal to 120 kcal per serving, 3 to 10 grams of total fat per serving, less than about 5 grams of saturated fat per serving, less than about 5 gram of trans fat per serving, less than about 6 grams of protein per serving, and less than about 20 grams of carbohydrates per serving.

22. The method of claim 21 wherein the second FMD nutrition bar is formulated from a combination of inulin, almond butter, brown rice crispy, cocoa powder, almonds, chocolate chips, rolled oats, brown rice syrup, flaxseed oil, rice dextrin, grape juice, and salt.

23. The method of claim 1, wherein the fasting-mimicking diet includes a drink that includes a glucose substitute.

24. The method of claim 1, wherein a refeeding diet is administered to the subject after the fasting-mimicking diet, the refeeding diet being a diet that provide an overall calorie consumption that is within 10 percent of a subject's normal calorie consumption.

25. The method of claim 24, wherein the fasting-mimicking diet and the refeeding diet are repeated for a plurality of cycles, each cycle being a sequence of the fasting-mimicking diet and the refeeding diet.

\* \* \* \* \*